United States Patent
Pedreira De Cerqueira Filho

(10) Patent No.: US 11,849,968 B2
(45) Date of Patent: Dec. 26, 2023

(54) FREE SCAR CARDIOVASCULAR CANNULA AND METHOD

(71) Applicant: Luiz Lanat Pedreira De Cerqueira Filho, Orlando, FL (US)

(72) Inventor: Luiz Lanat Pedreira De Cerqueira Filho, Orlando, FL (US)

(73) Assignee: Luiz Lanat Pedreira de Cerqueira Filho, Bahia (BR)

( * ) Notice: Subject to any disclaimer, the term of this patent is extended or adjusted under 35 U.S.C. 154(b) by 473 days.

(21) Appl. No.: 16/454,804

(22) Filed: Jun. 27, 2019

(65) Prior Publication Data

US 2020/0038055 A1    Feb. 6, 2020

Related U.S. Application Data

(63) Continuation-in-part of application No. 16/424,449, filed on May 28, 2019, now Pat. No. 11,471,186.

(60) Provisional application No. 62/789,515, filed on Jan. 7, 2019, provisional application No. 62/726,279, filed on Sep. 2, 2018, provisional application No. 62/690,822, filed on Jun. 27, 2018.

(51) Int. Cl.
```
A61B 17/34      (2006.01)
A61B 34/30      (2016.01)
A61B 17/00      (2006.01)
A61B 17/04      (2006.01)
```

(52) U.S. Cl.
CPC .... *A61B 17/3423* (2013.01); *A61B 17/00234* (2013.01); *A61B 17/3415* (2013.01); *A61B 17/3439* (2013.01); *A61B 34/30* (2016.02); *A61B 17/0469* (2013.01); *A61B 2017/00243* (2013.01); *A61B 2017/00349* (2013.01); *A61B 2017/00477* (2013.01); *A61B 2017/3425* (2013.01); *A61B 2017/3445* (2013.01)

(58) Field of Classification Search
CPC ................ A61B 17/3423; A61B 17/30; A61B 17/00234; A61B 17/3439
See application file for complete search history.

(56) References Cited

U.S. PATENT DOCUMENTS 4,695,273 A * 9/1987 Brown .................. A61M 39/10
                                                    604/173

* cited by examiner

*Primary Examiner* — Sameh R Boles

(57) ABSTRACT

An invention for connecting an extracorporeal circulation apparatus 35 to the patients' circulatory system 26B for providing extracorporeal blood circulation through a plurality of transfixions 44 in a tissue 25 space apart by a distance, comprising: a holder 10; and the plurality of ducts 14 connected to said holder 10; wherein said holder 10 is adapted to connect to the extracorporeal circulation apparatus 35; wherein at least one of said plurality of ducts 14 is adapted to connect to the patients' circulatory system 26B; wherein said holder 10 and said plurality of ducts 14 includes blood passageways 3. The invention including an internal connection 33 including a proximal portion 33A and a distal portion 33B; wherein said distal portion 33B is adapted to connect to the patients' circulatory system 26B; wherein said proximal portion 33A is connectable to said ducts 14. The methods are provided.

19 Claims, 23 Drawing Sheets

FIG. 20  FIG. 21
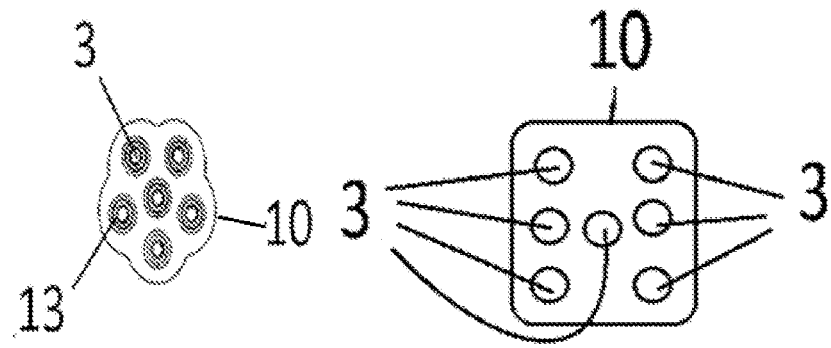
FIG. 22  FIG. 23
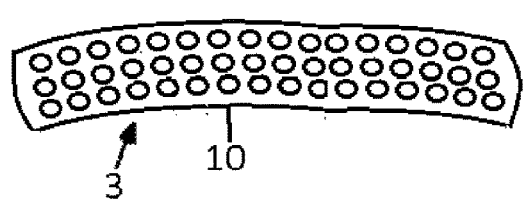 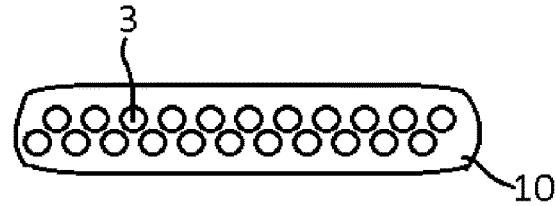
FIG. 24
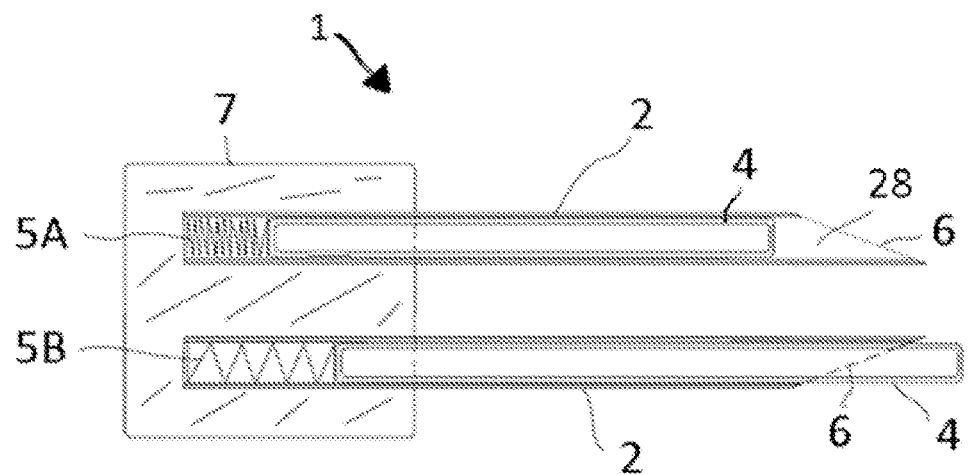

FREE SCAR CARDIOVASCULAR CANNULA AND METHOD

CROSS-REFERENCE TO RELATED APPLICATIONS

This application claims part of an invention which was disclosed in provisional application No. 62/690,822 filed 2018 Jun. 27, entitled "Thin cannulas trocar", and in application Ser. No. 62/726,279 filed 2018 Sep. 2, entitled "NoScarCardiacCannula and method" The benefit under 35 USC § 119(e) of the United States provisional application is hereby claimed, and the afore mentioned application is hereby incorporated herein by reference.

DESCRIPTION

Field of Invention

The invention is in the field of surgical devices and pertain, particularly, to a cardiovascular cannula 50 for connecting an extracorporeal circulation apparatus 35 to the patients' circulatory system 26B for providing extracorporeal blood circulation through a plurality of transfixions 44 in a tissue 25 to a surgical site 26.

Background

In the art of cardiovascular cannula for perform extracorporeal blood circulation also called cardiopulmonary bypass, many distinct types of cardiovascular cannula have been developed. One problem with the traditional cardiovascular cannula is to have a single cannula with thick outer diameter that damages the tissue. Another limitation of the current cardiovascular cannula is the need for an incision in the tissue generally with the use of a scalpel blade for the passage of a large caliber cannula. Another limitation of the current cardiovascular cannula is that the tissue incisions required for the passage of the trocar usually result in scars. Another limitation of the current cardiovascular cannula is to provide a single access passageway to the surgical site 26.

Current cardiovascular cannula for performing an extracorporeal blood circulation such as: open heart surgery, robot-assisted cardiac surgery, minimal invasive cardiac surgeries, among another, cause scars. These scars are not desired because, they alter the aesthetics of the body. The possibility of performing extracorporeal blood circulation without a scar is a grate evolution in surgery.

Therefore, what is clearly needed is a cardiovascular cannula 50 for connect an extracorporeal circulation apparatus 35 to the patients' circulatory system 26B for providing extracorporeal blood circulation through a plurality of transfixions 44 in a tissue 25 that the insertion into a surgical site 26 heals by first intention and leaves no visible scars on the tissue, and a method for use that solves the problems mentioned above.

SUMMARY OF THE INVENTION

In one embodiment of the invention, a cardiovascular cannula 50 for connect an extracorporeal circulation apparatus 35 to the patients' circulatory system 26B for extracorporeal blood circulation through a plurality of transfixions 44 including: a holder 10, a plurality of ducts 14 including a first end 14A and a first end 14B, the first end 14A connected to the holder, wherein the holder 10 and the plurality of ducts 14 includes a blood passageway 3, is provided.

Also, in another embodiment, the first end 14B is adapted to connect within a patients' circulatory system, is provided.

Also, in another embodiment, the holder 10 is adapted to connect to an extracorporeal circulation apparatus 35, is provided.

Also, in another embodiment, the holder 10 is modular and includes an external connection 36, the external connection 36 including a proximal end 36A and a distal end 36B, the proximal end 36A adapted to connect to an extracorporeal blood circulation apparatus 35, and the distal end 36B is adapted to detachably connect to the holder 10, is provided.

Also, in another embodiment, the plurality of ducts 14 is adapted for insertion through a trocar set 42 containing a plurality of access port 49.

Also, in another embodiment, the cardiac cannula, further comprising an internal connection 33, the internal connection 33 including a proximal portion 33A and a distal portion 33B, wherein the distal portion 33B is adapted to connect to the patients' circulatory system 26B, wherein the proximal portion 33A is adapted to connect to said ducts 14.

Also, in another embodiment, at least one of the plurality of ducts 14 further comprises a sharp tip 32 to transfix the tissue 25.

Also, in another embodiment, the plurality of ducts 14 is adapted to cause minimal trauma to the tissue in order to prevent scarring.

Also, in another embodiment, the cardiovascular cannula 50 assembly further comprising a mandrel 1, and the mandrel 1, including, a plurality of piercing tips 2 connected to a handle 7, wherein the mandrel 1 detachably engages the cannula 50 forming a single inserting trocar set 42.

Also, in another embodiment, at least one of the plurality of ducts 14 comprises a beater 27.

Also, in another embodiment, at least one part is made in a transparent material.

Also, in another embodiment, at least one of the plurality of ducts 14 is adapted to connect a surgical device 52 within the surgical site 26.

Also, in another embodiment, the plurality of ducts 14 comprises means for keeping the blood passageway 3 open through the cardiovascular cannula 50.

Also, in another embodiment, the cardiovascular cannula 50 assembly further comprising a protector guide 8.

Also, in another embodiment, at least one of the plurality of ducts 14, further comprises a fastening system 47 in the tissue.

Also, in another embodiment, the cardiovascular cannula 50 assembly further comprising at least one modular part 54 adapted to connect another modular part 54.

Also, in another embodiment, at least one of the pluralities of piercing tips 2 comprises a retractable 4 protection system.

Also, in another embodiment, at least one of the plurality of ducts 14 are adapted to connect to an internal connection 33 in the surgical site 26.

Also, in another embodiment, the holder 10 is adapted to connect to a surgical device 52.

Also, in another embodiment, the cardiovascular cannula 50 assembly, further comprising at least one the modular part 54 is adapted to connect to the extracorporeal circulation apparatus 35.

In another embodiment, the extracorporeal circulation cannula 50 for connecting an extracorporeal circulation apparatus 35 to the patients' circulatory system 26B for extracorporeal blood circulation through a plurality of transfixions 44 in the tissue 25 space apart by a distance, including: a holder 10 adapted to connect to an extracorporeal circulation apparatus 35, a plurality of ducts 14 connected to the holder 10, and an internal connection 33 adapted to connect the plurality of ducts 14 within the patients' circulatory system 26B, is provided.

Also, in another embodiment, the internal connection 33 is adapted to be inserted in the surgical site 26 through a conventional trocar 53.

Also, in another embodiment, the internal connection 33 includes means to fix in the cardiovascular tissue 25B.

Also, in another embodiment, further comprising a mandrel 1, and the mandrel 1 including a plurality of piercing tips 2 connected to a handle 7, wherein the mandrel 1 detachably engages the cannula, forming a single punch trocar set 42.

A method for extracorporeal circulation, including: inserting a plurality of ducts 14 of a cardiovascular cannula 50 into a surgical site 26 through a plurality of transfixions 44 in the tissue 25, connecting the cardiovascular cannula 50 to a patients' circulatory system 26B, connecting the cardiovascular cannula 50 to an extracorporeal circulation apparatus 35, inserting a second cardiovascular cannula 50 into a surgical site 26, connecting the second cardiovascular cannula 50 to a patients' circulatory system 26B, connecting the second cardiovascular cannula 50 to an extracorporeal circulation apparatus 35, perform an extracorporeal circulation, is provided.

Also, the method, further including, connecting an internal connection 33 to the plurality ducts 14, is provided.

Also, the method, further including, removing the cardiovascular cannula 50 of a patients' circulatory system 26B and removing the second cardiovascular cannula 50 of a patients' circulatory system 26B, is provided.

BRIEF DESCRIPTION OF THE DRAWINGS

FIG. 20-21 are top views of some embodiments of the invention showing: some holder 10 shape, some position of the blood passageways 3 in the holder 10, and some distribution of the blood passageways 3 in the holder 10.

FIG. 22 and FIG. 23 are top views of some embodiments of the invention adapted for insertion of the intercostal space.

FIG. 24 is a cross-sectional view of the mandrel 1 wherein two piercing tips 2 comprise the retractable 4 protection system, according to another embodiment invention.

DETAILED DESCRIPTION OF THE PREFERRED EMBODIMENTS

The inventor provides a cardiovascular cannula 50 for extracorporeal blood circulation that the insertion into a surgical site 26 heals by first intention and leaves no visible scars on the tissue, and a method for use.

The inventor provides a cardiovascular cannula 50 for providing a plurality of transfixions 44 through a tissue into a surgical site 26 and whose punctures site in the tissue heals by first intention and leaves no visible scars on the tissue, and a method for use that solves the problems mentioned above.

The invention is described in enabling detail in the following examples, which may represent more than one embodiment of the invention, together with the accompanying drawings in which like numerals represent similar components. Additionally, the structures described herein can be embodied as integrated components or as separate components.

Figure 1:
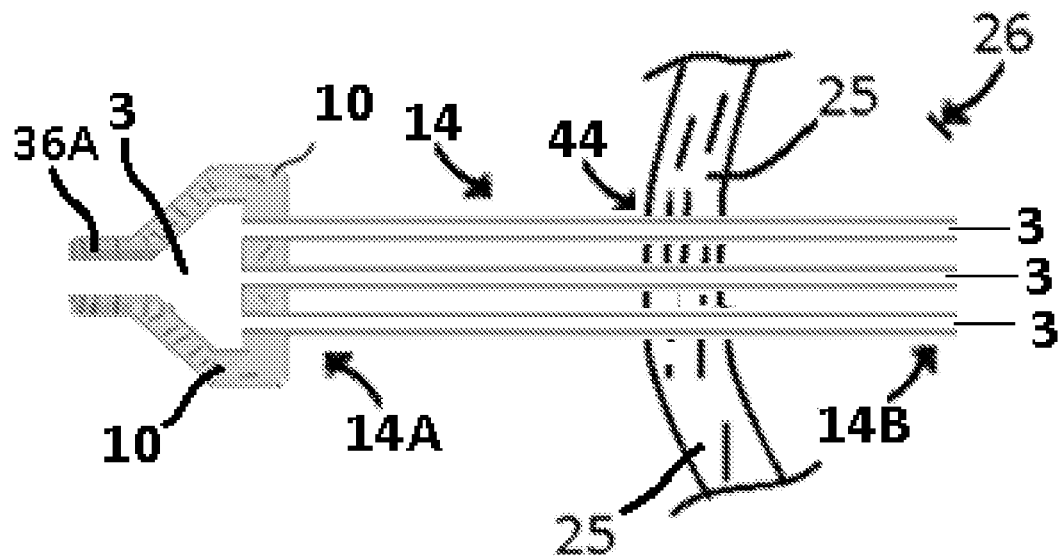
FIG. 1 is site cross sectional view of the cardiovascular cannula 50 assembly for insertion into the surgical site 26 through the plurality of transfixions 44 in the tissue 25 space apart by a distance, according to one embodiment of the invention.

FIG. 1 is a cross sectional view of the cardiovascular cannula 50 assembly for insertion into a surgical site 26 through the plurality of a transfixions 44 in a tissue 25, according to one embodiment of the invention.

In another characteristic of this embodiment, a holder 10; the plurality of a ducts 14 including a first end 14A and a second end 14B, the first end 14A connected to the holder 10; wherein the holder 10 and the ducts 14 including a blood passageway 3.

Figure 2:
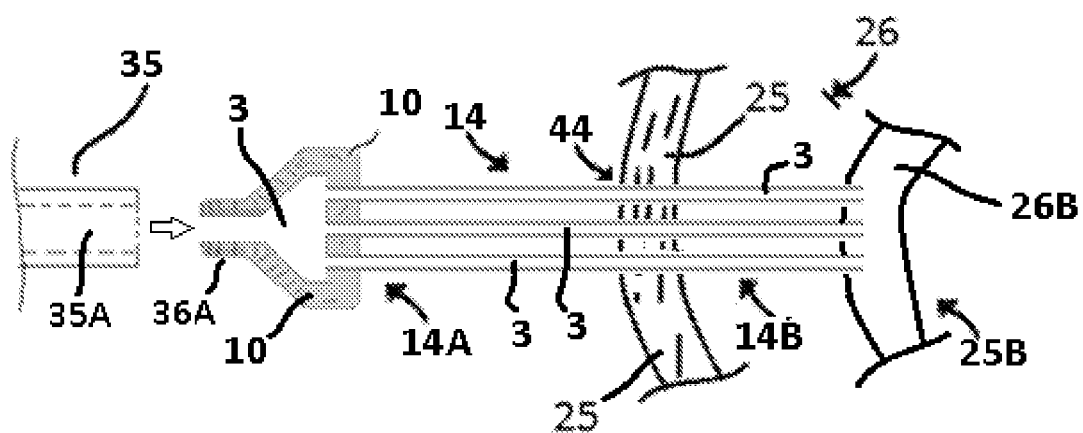
FIG. 2 is a cross sectional view of the cardiovascular cannula 50 for extracorporeal blood circulation transfixing a plurality of ducts 14 in a tissue 25 connecting an extracorporeal circulation apparatus 35 to the patients' circulatory system 26B through the plurality of transfixions 44 in the tissue 25, according to another embodiment of the invention.

FIG. 2 is a cross sectional view of the cardiovascular cannula 50 assembly for the insertion into the surgical site 26 through the plurality of transfixions 44 in the tissue 25, according to another embodiment of the invention.

This embodiment includes the holder 10; the plurality of ducts 14 including the first end 14A and the second end 14B, the first end 14A connected to the holder 10; wherein the holder 10 and the ducts 14 include the blood passageway 3.

In another characteristic of this embodiment, the second end 14B is adapted to connect within a patients' circulatory system 26B.

In another characteristic of this embodiment, the holder 10 is adapted to connect to an extracorporeal circulation apparatus 35 hose. In another characteristic of this embodiment, the holder 10 includes a fit 10A to connect to the extracorporeal circulation apparatus 35 hose. In another characteristic of this embodiment, the arrow shows the direction that the extracorporeal circulation apparatus 35 hose connects to a proximal end 36A.

Figure 3:
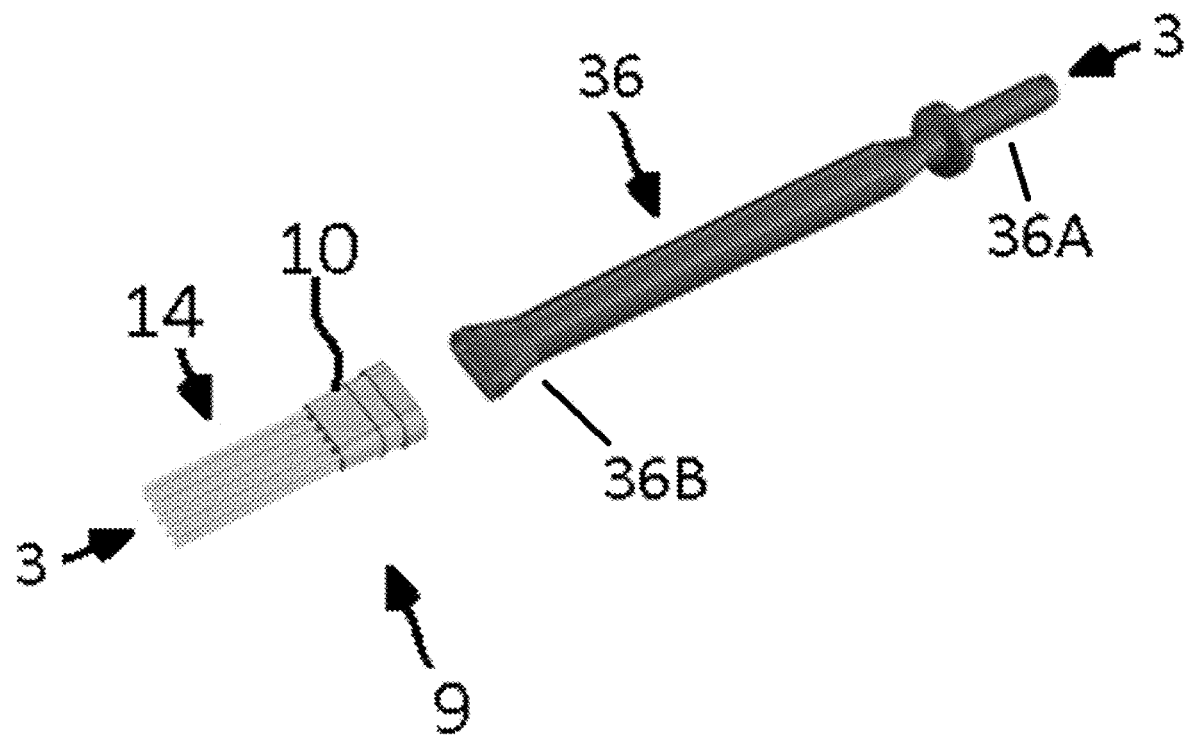
FIG. 3 is a perspective view of the cardiovascular cannula 50 assembly for insertion into the surgical site 26 through the plurality of transfixions 44 in the tissue 25, according to another embodiment of the invention.

FIG. 3 is a perspective view of the cardiovascular cannula 50 assembly for insertion into the surgical site 26 through the plurality of transfixions 44 in the tissue 25, according to another embodiment of the invention.

This embodiment includes the holder 10; the plurality of ducts 14 including the first end 14A and the second end 14B, the first end 14A connected to the holder 10; wherein the holder 10 and the ducts 14 including the blood passageway 3.

In another characteristic of this embodiment, the holder 10 is modular, including an external connection 36. In another characteristic of this embodiment, the external connection 36 includes the proximal end 36A and a distal end 36B.

In another characteristic of this embodiment, the holder 10 is modular, including the external connection 36, the external connection 36, including the proximal end 36A and the distal end 36B. The proximal end 36A is adapted to connect to the extracorporeal circulation apparatus 35, and the distal end 36B is adapted to detachably connect to the holder 10.

In another characteristic of this embodiment, a middle part 9 includes the holder 10 and the plurality of ducts 14. In another characteristic of this embodiment, the distal end 36B is adapted to detachably connect to the holder 10. In another characteristic of this embodiment, the distal end 36B is adapted to detachably connect to the middle part 9 in a sealing manner to avoid the escape of blood and the entrance of air in the extracorporeal blood circulation circuit. In another characteristic of this embodiment, the proximal end 36A is designed to connect to the extracorporeal circulation apparatus 35 hose.

In another characteristic of this embodiment, the plurality of ducts 14 are adapted to transfix the tissue 25, reach the surgical site 26, transfix a cardiovascular tissue 25B and reach the patients circulatory system 26B.

Figure 4:
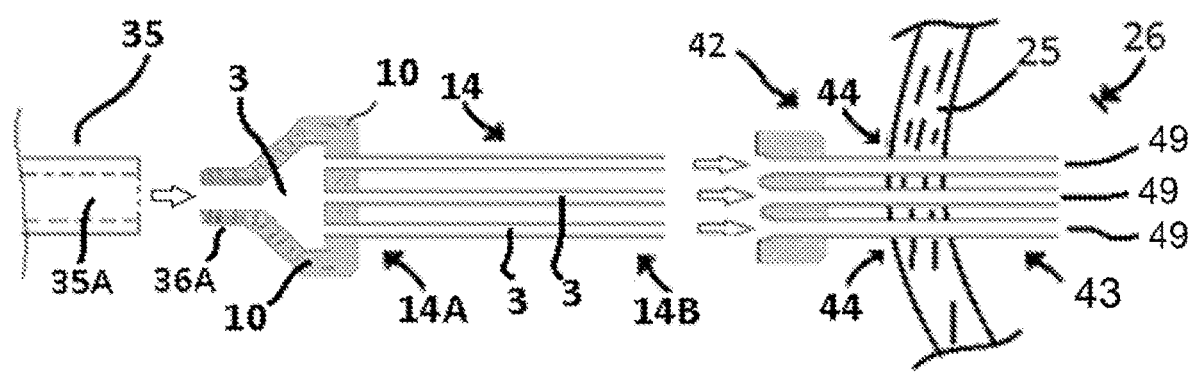
FIG. 4 is a cross sectional view of trocar ser 42 adapted to provide a plurality of transfixions 44 in the tissue 25 for insertion of the cardiovascular cannula 50 assembly into the surgical site 26, according to another embodiment of the invention.

FIG. 4 is a cross sectional view of a trocar set 42, adapted to provide a plurality of transfixions 44 in the tissue 25 for the insertion of the cardiovascular cannula 50 assembly into the surgical site 26, according to another embodiment of the invention.

In another characteristic of this embodiment, the plurality of ducts 14 is adapted for insertion through the trocar set 42 containing a plurality of tubes 43. In another characteristic of this embodiment, the plurality of ducts 14 is adapted to cause minimal trauma to the tissue 25 to prevent scars. Another characteristic of this embodiment is that the trocar set 42 provides three access port 49, for the insertion of the ducts 14 in the surgical site 26. In another characteristic of this embodiment, the trocar set 42 is adapted to cause minimum trauma in the tissue 25 to prevent scars.

Figure 5:
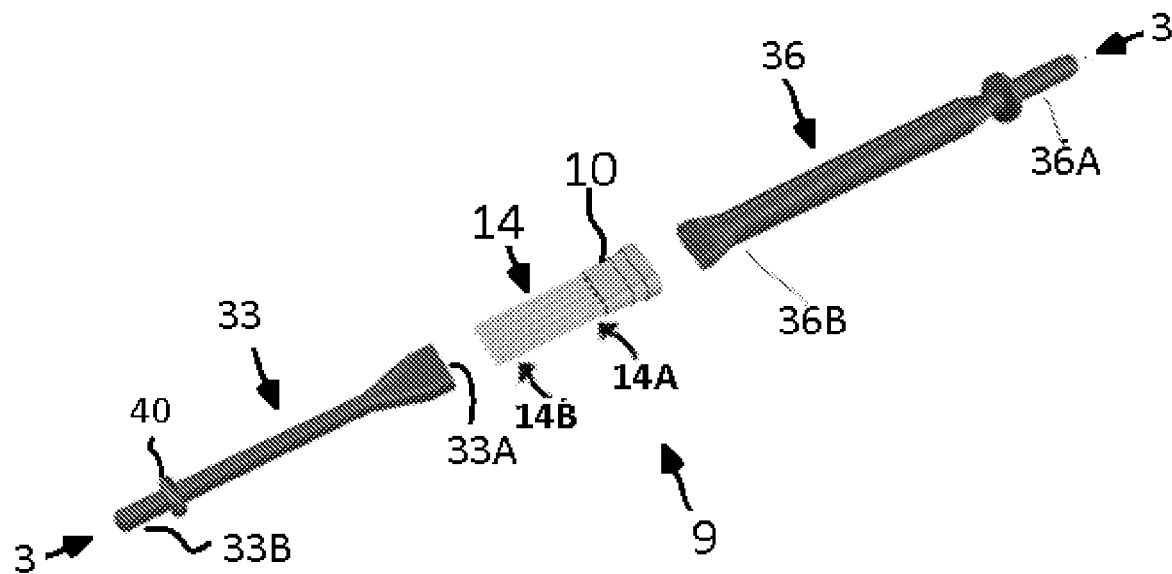
FIG. 5 is a perspective view of another embodiment of the invention including the internal connection 33.

FIG. 5 is a perspective view of another embodiment of the invention, including the internal connections 33.

This embodiment, includes an internal connection 33, which includes a proximal portion 33A and a distal portion 33B, wherein the distal portion 33B is adapted to connect to the patients' circulatory system 26B, wherein the proximal portion 33A is adapted to detachably connect to the second end 14B; wherein the internal connection 33 accesses the surgical site 26 by another access route.

In another characteristic of this embodiment, the internal connection 33 accesses the surgical site 26 by another access route, such as, for example, a conventional trocar 53 or a surgical incision, but is not limited to them.

In another characteristic of this embodiment, the external connection 36 is adapted to detachably connect the holder 10, and the internal connection 33 is adapted to detachably connect the plurality of ducts 14 to form the single cardiovascular cannula 50 assembly.

In another characteristic of this embodiment, the external connection 36 is disconnected from the holder 10, and the plurality of ducts 14 is disconnected from the proximal portion 33A of the internal connection 33.

In another characteristic of this embodiment, the distal end 36B is adapted to connect disconnect ably to the holder 10. In another characteristic of this embodiment, the connection of the distal end 36B in the holder 10 is of a sealant form so that there is no blood leakage and air intake in the blood flow. In another characteristic of this embodiment, a ring 40 limits the transfixions 44 of the distal portion 33B to the patients' circulatory system 26B. In another characteristic of this embodiment, the proximal end 36A is designed to connect to the extracorporeal circulation apparatus 35 hose. In another characteristic of this embodiment, the middle part 9 includes the holder 10 and the plurality of ducts 14. In some embodiments, the middle part 9 is the trocar set 42 including a sharp tip 32. In some embodiments the middle part 9 is the trocar set 42 and has a mandrel 1 including the piercing tip 2 to insert in the tissue 25. In some embodiments the middle part 9 is made to be inserted through the access ports 49 of the trocar set 42. In another characteristic of this embodiment, the trocar set 42 includes the plurality of a tubes 43. In another characteristic of this embodiment, the number of ducts 14 required to maintain adequate blood flow for the extracorporeal circulation apparatus 35 and the various embodiments depends on the size of the plurality of ducts 14, the length of the plurality of ducts 14, the diameter of the plurality of ducts 14 and the volume of blood required. In some embodiments, the number of plurality of ducts 14 may be altered during the procedure to match the necessary blood flow to the patients' circulatory system 26B. In some embodiments, the number of plurality of ducts 14 is adapted to be altered during the procedure to match the blood flow necessary for the patients' circulatory system 26B by adding or reducing the number of ducts 14 used for the passage of blood.

Figure 6:
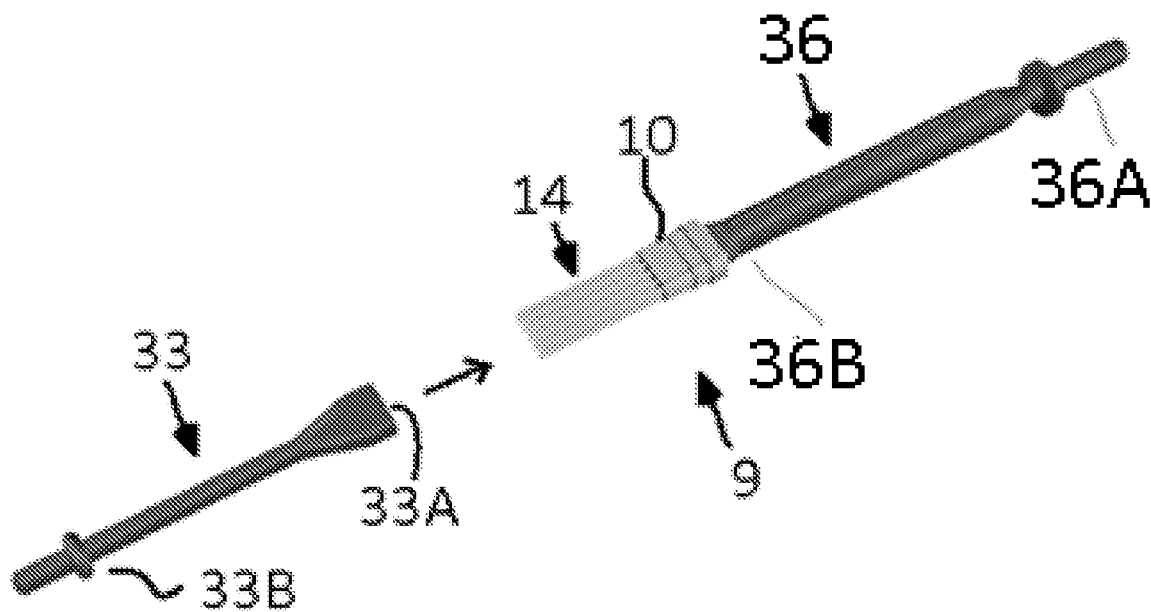
FIG. 6 is a perspective view of the external connection 36 connect to the holder 10 and including the internal connection 33, according to another embodiment of the invention.

FIG. 6 is a perspective view of the external connection 36 connected to the holder 10 and including the internal connection 33, according to another embodiment of the invention.

In another characteristic of this embodiment, the holder 10 is made of one material and the external connection 36 is made of another material.

In this embodiment, the internal connection 33 includes the proximal portion 33A and the distal portion 33B, wherein the distal portion 33B is adapted to connect to the patients' circulatory system 26B, wherein the proximal portion 33A is adapted to connect to the second end 14B; wherein the internal connection 33 accesses the surgical site 26 by another access route. The internal connection 33 accesses the surgical site 26 by another access route, such as, for example, a conventional trocar 53 or a surgical incision, but is not limited to them.

In another characteristic of this embodiment, the proximal end 36A is adapted to connect to the extracorporeal circulation apparatus 35 hose.

In another characteristic of this embodiment, the arrow points the direction in which the internal connection 33 connects to the plurality of ducts 14. In some embodiments, the middle part 9 and the external connection 36 are a single piece. In some embodiments there are no external connection 36, the extracorporeal circulation apparatus 35 hose is adapted to connect directly to the holder 10.

Figure 7:
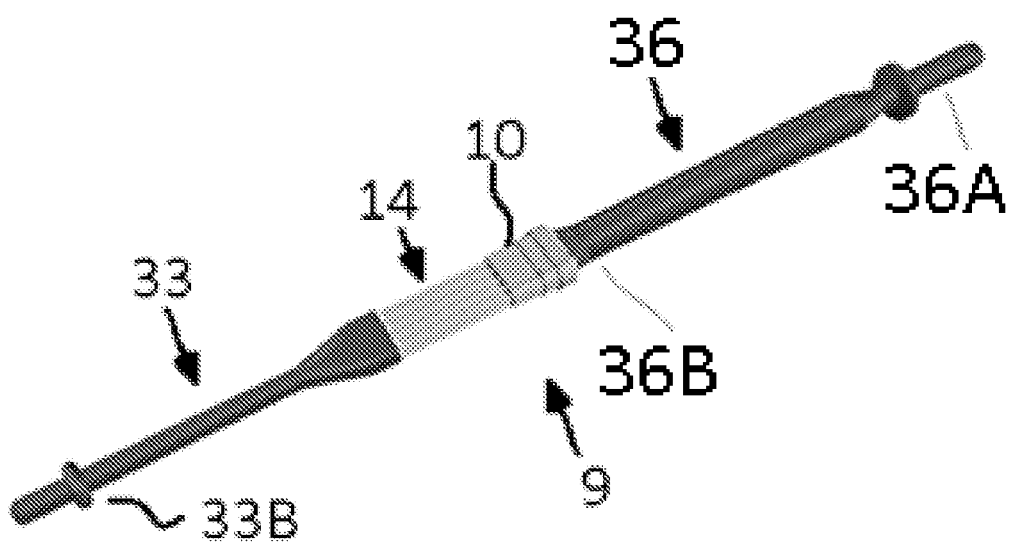
FIG. 7 is a perspective view of the functional cardiovascular cannula 50 assembly, according to one embodiment of the invention.

FIG. 7 is a perspective view of the functional cardiovascular cannula 50 assembly, according to one embodiment of the invention.

In another characteristic of this embodiment, the invention is modular, the external connection 36 is connected to the middle part 9, and the middle part 9 is connected to the internal connection 33, forming the cardiovascular cannula 50 assembly. In another characteristic of this embodiment, the middle part 9 includes the holder 10 and the plurality of ducts 14. In another characteristic of this embodiment, the external connection 36 is adapted to detachably connect to the holder 10 of the middle part 9, and the internal connection 33 is adapted to detachably connect the plurality of ducts 14 to form the single cardiovascular cannula 50 assembly. In another characteristic of this embodiment, the distal end 36B is detachably connected to the holder 10 of the middle part 9. In another characteristic of this embodiment, the connection of the distal end 36B in the holder 10 has a sealing shape so that there is no leakage of blood and inflow of air into the extracorporeal circulation blood flow. In another characteristic of this embodiment, the proximal end 36A is designed to connect to the extracorporeal circulation apparatus 35 hose.

Figure 8:
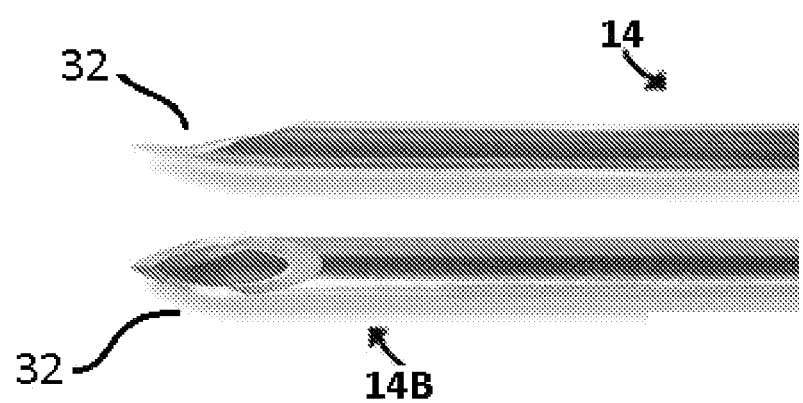
FIG. 8 is a lateral view of the second end 14B including piercing sharp tip 32, according to another embodiment of the invention.

FIG. 8 is a lateral view of the second end 14B, including the sharp tip 32 piercing, according to another embodiment of the invention.

In another characteristic of this embodiment, the plurality of ducts 14 are adapted to cause minimal trauma to the tissue 25 to prevent scarring.

In another characteristic of this embodiment, at least one of the plurality of ducts 14 further includes a sharp tip 32 in the second end 14B to insert in the tissue 25.

In one characteristic of some embodiments, the ducts 14 have sharp tip 32 to puncture de tissue 25. In another characteristic of this embodiment, the second end 14B is adapted to connect to the internal connection 33. In another characteristic of this embodiment, the ducts 14 are adapted to leave no scar on the skin. In another characteristic of this embodiment, the sharp tip 32 is adapted to cause minimal trauma to the tissue 25 to not leave any scars in the tissue 25. In another characteristic of this embodiment, the sharp tip 32 easily penetrates the tissue 25 and causes no scars. In another characteristic of this embodiment, the smaller the external diameter of the ducts 14, lower is the risk of scarring by perforation.

Figure 9:
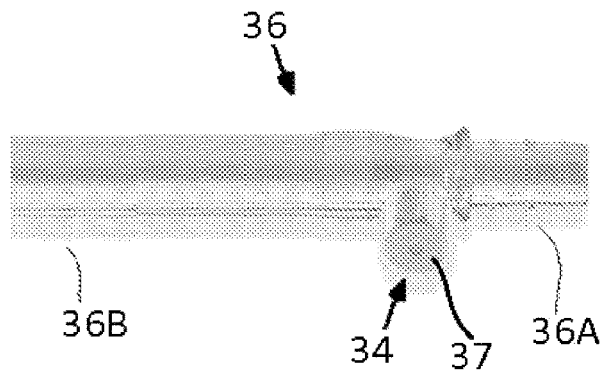
FIG. 9 a perspective view of the external connection 36 according to another embodiment of the invention.

FIG. 9 is a perspective view of the external connection 36, according to another embodiment of the invention.

In this embodiment, the external connection 36 has the distal end 36B and the proximal end 36A. In another characteristic of this embodiment, the proximal end 36A is designed to connect to the extracorporeal circulation apparatus 35 hose. In another characteristic of this embodiment, the distal 32B is designed to fit the sealing into the holder 10. In another characteristic of this embodiment, the external connection 36 has a side connection 34. In another characteristic of this embodiment, the screw a cap 37 is connected to the side connections 34. In another characteristic of this embodiment, the side connections 34 is an access to the blood flow for delivering medications, measure blood pressure and collecting blood but is not limited to them.

Figure 10:
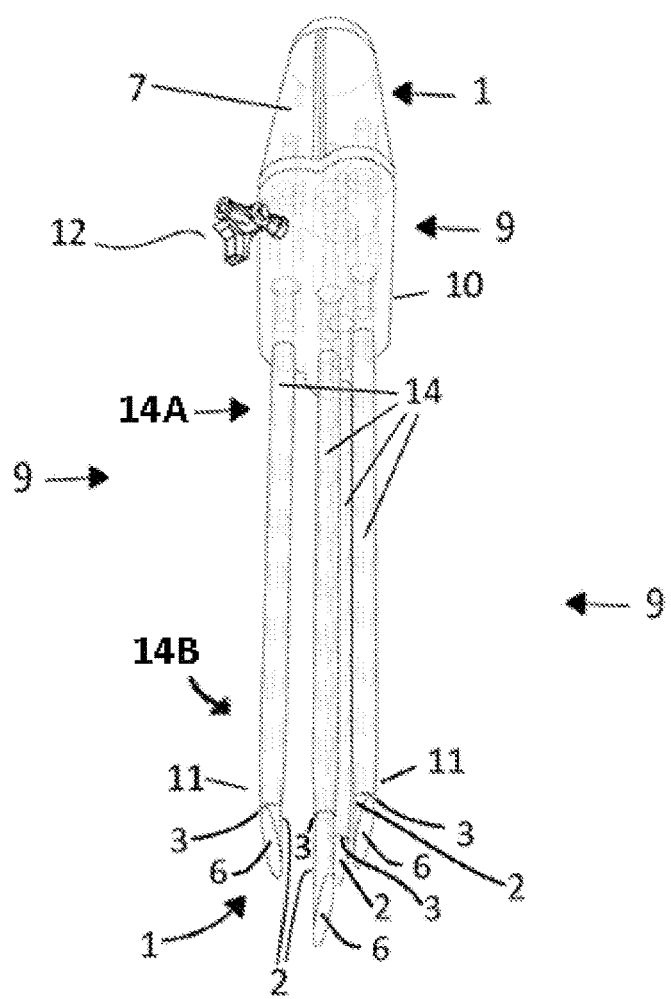
FIG. 10 is a perspective view of the invention including the mandrel 1, according to another embodiment of the invention.

FIG. 10 is a perspective view of the invention including the mandrel 1, according to another embodiment of the invention.

In another characteristic of this embodiment, the mandrel 1 includes the plurality of a piercing tips 2 connected to a handle 7, wherein the mandrel 1 detachably engages the cardiac cannula forming the single inserting trocar set 42.

In another characteristic of this embodiment, it contains: the mandrel 1, and the mandrel 1 including the plurality of piercing tips 2 connected to the handle 7, wherein the mandrel 1 detachably engages the middle part 9, forming a single set. This embodiment provides four blood passageways 3 through the tissue 25 to the surgical site 26.

In another characteristic of this embodiment, the holder 10 is adapted to connect to the external connection 36. In another characteristic of this embodiment, the plurality of ducts 14 is adapted to connect to the internal connection 33.

In another characteristic of this embodiment, the surgeon uses the invention in a single punch assembly to puncture the tissue 25, the trocar set 42 transfixes the tissue 25 at four different points until each plurality of ducts 14 reaches the surgical site 26. In another characteristic of this embodiment, each piercing tips 2 is solid and has a bezel 6 shaped tip to facilitate the insertion in the tissue 25. In another characteristic of this embodiment, each duct 14 has four blood passageways 3 and the four piercing tips 2 that are engaged in the four blood passageways 3.

In another characteristic of this embodiment, longitudinally sliding the mandrel 1 relative to the middle part 9 fully detaches the mandrel 1 of the middle part 9. In another characteristic of this embodiment, after the tissue 25 has been transfixed, the surgeon removes the mandrel 1 from the middle part 9. In another characteristic of this embodiment, the middle part 9 remains in the tissue 25 during surgery, so that each duct 14 of the plurality of ducts 14 has an independent blood passageway 3 through the tissue 25 to the surgical site 26, where surgery will be performed. In another characteristic of this embodiment, each duct 14 of the plurality of ducts 14 has the blood passageway 3.

In another characteristic of this embodiment, the plurality of ducts 14 is adapted to cause minimal trauma to the tissue 25, to prevent scar formation in the tissue 25. In another characteristic of this embodiment, the plurality of ducts 14 has an outer diameter which is adapted to prevent scar formation in the tissue 25. In another characteristic of this embodiment, the outer diameter is thin enough to cause minimal trauma to the tissue 25, to avoid scars at the insertion site. In another characteristic of this embodiment, the piercing tips 2 have the bezel 6 sharp to, easily, penetrate the tissue 25 and not cause scars. In another characteristic of this embodiment, the smaller the external diameter of the cannula ducts 14, the lower is the risk of scars by perforation.

In another characteristic of this embodiment, it is widely known that the use of needles to deliver medication, including syringes, leaves no scar on the tissue 25. In another characteristic of this embodiment, the thin needle causes small damage to the tissue 25, that regenerates by first intention without leaving a scar. In another characteristic of this embodiment, it works substantially comparable to a plurality of needles, inserting different points of the tissue 25 at the same time. In another characteristic of this embodiment, instead of incising the tissue 25 to insert into the surgical site 26, a conventional trocar 53, which requires a large incision in the tissue 25, the tissue 25 is punctured by this embodiment of the invention, which has the plurality of piercing tips 2. Each covered by the plurality of ducts 14; each piercing tip 2 of the trocar set 42 assembly pierces the tissue 25 and transfixes the tissue 25 until it reaches the surgical site 26. In another characteristic of this embodiment, the tissue 25 insertion of the ducts 14 with the piercing tips 2 is engaged to function, substantially, similar to the insertion of an injection needle of a syringe. Also, this embodiment functions, substantially, similar to the insertion of a vein insertion catheter that does not cause scar.

In another characteristic of this embodiment, at least, one of the plurality of ducts 14 comprises the second end 14B adapted to dilate an insertion hole in the tissue 25 to prevent scars.

In another characteristic of this embodiment, the four plurality of ducts 14 comprises, in the second end 14B, a dilator 11 adapted to dilate an insertion hole in the tissue 25. In another characteristic of this embodiment, at the second end 14B of each plurality of ducts 14, there is the conical shaped dilator 11, which dilates the insertion hole made by the piercing tips 2 in the tissue 25. In another characteristic of this embodiment, this allows the punch into the tissue 25 with the plurality of ducts 14 with an outer diameter greater than the insertion hole made by the piercing tip 2 without causing scars. In another characteristic of this embodiment, the trocar set 42 assembly performs four insertions on the tissue 25. Each insertion includes a small diameter that leaves no scar on the tissue 25. After the trocar set 42 is removed from the tissue 25, the dilated punching orifice retracts, remaining on the tissue 25 only small insertions, which do not cause scars and do not need to be treated, including suture.

In another characteristic of this embodiment, at least, one part is made of a transparent material.

In another characteristic of this embodiment, the trocar set 42 is made of a transparent material that allows a view of what is in its internal parts during the video-surgery.

In another characteristic of this embodiment, the middle part 9 has a faucet 12 for collecting blood and ministering medications by the blood passageways 3 of the plurality of ducts 14. In another characteristic of this embodiment, the faucet 12 controls the inlet and outlet of blood from the surgical site 26, the faucet 12 communicates with at least one blood passageways 3 of the four plurality of ducts 14 and allows to inflate liquids in and blood out of the patients' circulatory system 26B, in accordance with another embodiment of the invention.

In another characteristic of some embodiments of the invention, the mandrel 1 comprises two piercing tips 2; in some embodiments of the invention, the mandrel 1 comprises three piercing tips 2; n some embodiments of the invention, the mandrel 1 comprises four piercing tips 2; in some embodiments of the invention, the mandrel 1 comprises five piercing tips 2; in some embodiments of the invention, the mandrel 1 comprises six piercing tips 2; in some embodiments of the invention, the mandrel 1 comprises seven piercing tips 2; in some embodiments of the invention, the mandrel 1 comprises eight piercing tips 2; in some embodiments of the invention, the mandrel 1 comprises nine piercing tips 2; in some embodiments of the invention, the mandrel 1 comprises ten piercing tips 2; in some embodiments of the invention, the mandrel 1 comprises eleven piercing tips 2; in some embodiments of the invention, the mandrel 1 comprises twelve piercing tips 2; in some embodiments of the invention, the mandrel 1 comprises thirteen piercing tips 2; In some embodiments of the invention, the mandrel 1 comprises fourteen piercing tips 2, but the number of piercing tips 2 is not limited to them.

In some embodiments, the invention comprises two ducts 14; in some embodiments, the invention comprises three ducts 14; in some embodiments, the invention comprises four ducts 14; in some embodiments, the invention comprises five ducts 14; in some embodiments, the invention comprises six ducts 14; in some embodiments, the invention comprises seven ducts 14; in some embodiments, the invention comprises eight ducts 14; in some embodiments, the invention comprises nine ducts 14; in some embodiments, the invention comprises ten ducts 14; in some embodiments, the invention comprises eleven ducts 14; in some embodiments, the invention comprises twelve ducts 14; in some embodiments, the invention comprises thirteen ducts 14; in some embodiments, the invention comprises fourteen ducts 14, but the number of ducts 14 are not limited to them.

Figure 11:
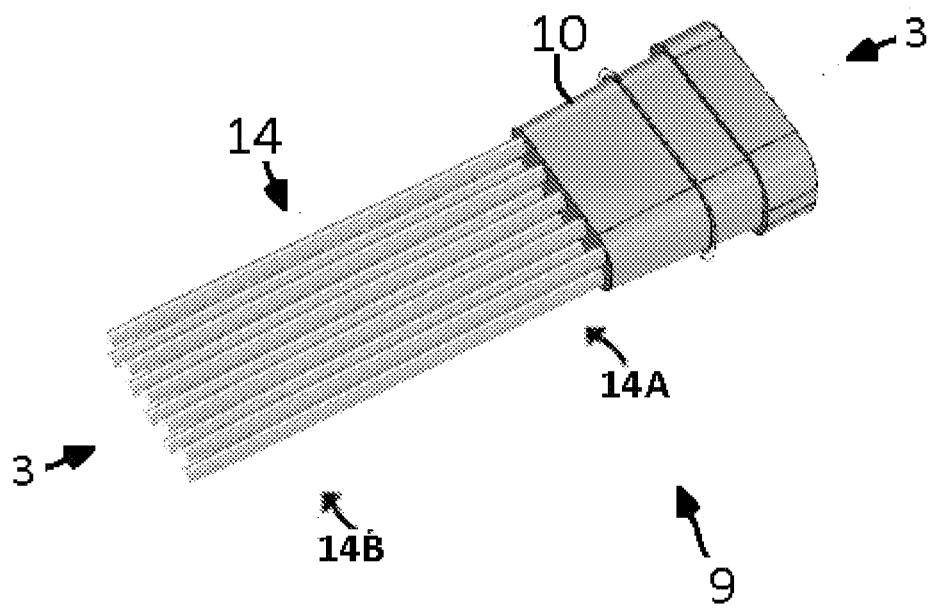
FIG. 11 is a perspective view of the middle part 9 including ten ducts 14, according to another embodiment of the invention.

FIG. 11 is a perspective view of the middle part 9 including ten ducts 14, according to other embodiments of the invention.

In another characteristic of this embodiment, the ten ducts 14 are arranged in two lines of five ducts 14 in a formation suitable for transfixing the tissue 25 in the intercostal space. In another characteristic of this embodiment, the holder 10 of the middle part 9 is designed to fit sealing to the distal end 36B of the external connection 36, the plurality of ducts 14 is designed to fit, quickly and securely, in the distal portion 33B. In some embodiments, the plurality of ducts 14 are made to pass through the trocar set 42, including the plurality of blood passageways 3. In some embodiments, the plurality of ducts 14 are made to pass through the plurality of blood passageways 3 in the tissue 25. In some embodiments, the middle part 9 is made to be inserted through the trocar set 42 including the plurality of ducts 14. In some embodiments, the middle part 9 is the trocar set 42 and it is made to, directly, insert the tissue 25. In some embodiments, the middle part 9 is the trocar set 42 and has the mandrel 1 to insert the tissue 25.

Figure 12:
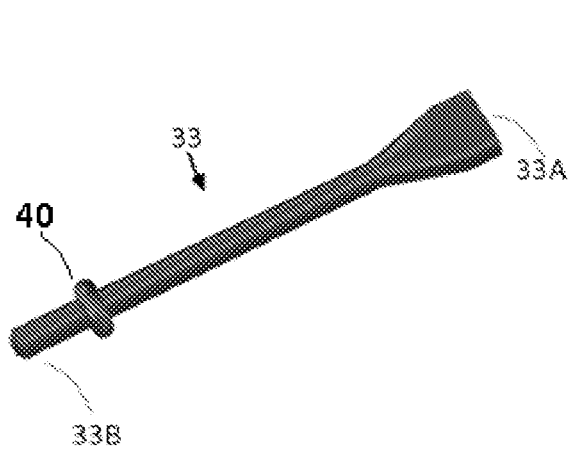
FIG. 12 is a perspective view of the internal connection 33 according to another embodiment of the invention.

FIG. 12 is a perspective view of the internal connection 33, according to another embodiment of the invention.

In another characteristic of this embodiment, the internal connection 33 is designed to be inserted into the surgical site 26 from within the conventional trocar 53, a surgical incision, but it is not limited to them. In another characteristic of this embodiment, the internal connection 33 is made to function in the surgical site 26.

In another characteristic of this embodiment, the proximal portion 33A of the internal connection 33 is adapted to connect to the second end 14B inside the surgical site 26.

In another characteristic of this embodiment, at least, one of the plurality of ducts 14 is adapted to connect a surgical device 52 within the surgical site 26.

In some embodiments, the invention has an adapter 38 (it is not on the drawing) to connect the plurality of ducts 14 to the internal connection 33. In some embodiments, the proximal portion 33A of the internal connection 33 is adapted to connect to the adapter 38 inside the surgical site 26. In some embodiments, the adapter 38 is adapted to connect to the plurality of ducts 14 and the internal connection 33 is connected to the adapter 38.

In another characteristic of this embodiment, the internal connection 33 may be made in various shapes, sizes, and models. In another characteristic of this embodiment, the distal portion 33B is adapted to be inserted into the patients' circulatory system 26B. In another characteristic of this embodiment, the distal portion 33B is adapted to be inserted into the patients' circulatory system 26B, for example: heart cavity, aorta, vena cava, but are not limited to them.

Figure 13:
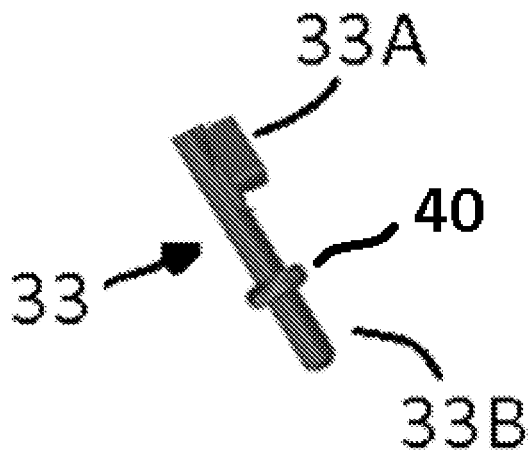
FIG. 13 is a perspective view of the internal connection 33, the distal portion 33B connection is lateral. according to another embodiment of the invention.

FIG. 13 is a perspective view of the internal connection 33, where the distal portion 33B connection is lateral, according to another embodiment of the invention.

In another characteristic of this embodiment, the distal portion 33B is adapted to connect sideways to a fitting 30 (not shown) of the ducts 14.

In another characteristic of this embodiment, the side portion of the distal portion 33B is adapted to connect to the second end 14B of the plurality of ducts 14. In another characteristic of this embodiment, it is adapted to pass, easily, through a conventional trocar 53.

In another characteristic of this embodiment, the proximal portion 33A is designed to fit quickly and sealing on the plurality of ducts 14B, according to another embodiment of the invention.

Figure 14:
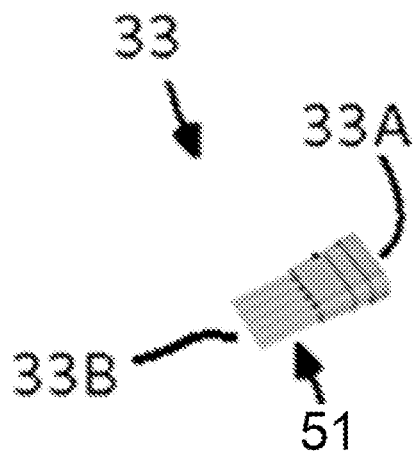
FIG. 14 is a perspective view of the internal connection 33 including the plurality of pipe 51 according to another embodiment of the invention.

FIG. 14 is a perspective view of the internal connection 33, including the plurality of pipes 51, according to another embodiment of the invention.

In another characteristic of this embodiment, the internal connection 33 includes the pipes 51 that includes a sleeve 45 including the plurality of pipes 51. In another characteristic of this embodiment, the plurality of pipes 51 includes the plurality of blood passageways 3 to the patients' circulatory system 26B. In another characteristic of this embodiment, the internal connection 33 is adapted to insert the cardiovascular tissue 25B at a plurality of sites, so as to connect an extracorporeal circulation blood flow 35A to the patients' circulatory system 26B. In another characteristic of this embodiment, the patients' circulatory system 26B is the surgical site 26 existing within an organ having blood flow, such as, for example: inside the aorta artery, inside the vena cava, inside the heart, but is not limited to them. In another characteristic of this embodiment, this embodiment is adapted to pass through a conventional trocar 53.

Figure 15:
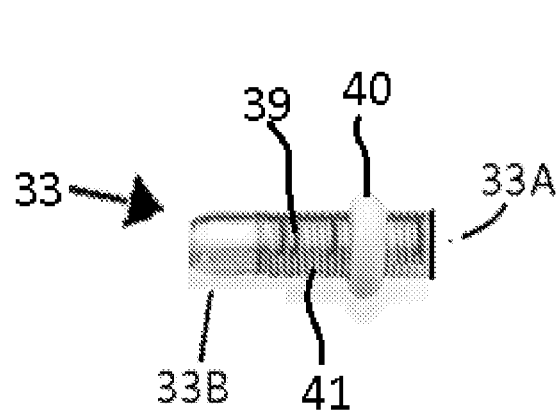
FIG. 15 is a side view of the internal connection 33, including: the ring 40, the spring 41, and the markings 39, according to another embodiment of the invention.

FIG. 15 is a side view of the internal connection 33, including: the ring 40, a spring 41, and a marking 39, according to another embodiment of the invention.

In another characteristic of this embodiment, the ring 40 is movable on the internal connection 33 and serves as a stop for the internal connection 33 inlet in the patients' circulatory system 26B. The markings 39 serves as a measure for how much of the internal connections 33 enters the patients' circulatory system 26B.

In another characteristic of this embodiment, the plurality of cannulas comprises means for keeping the blood passage open through the cannula.

In another characteristic of this embodiment, the invention comprises means for maintaining open the passage of blood, the spring 41 keeps the blood passageways 3 always open for the blood flow. In some embodiments, there are metal rings, throat, but is not limited to them.

Figure 16:
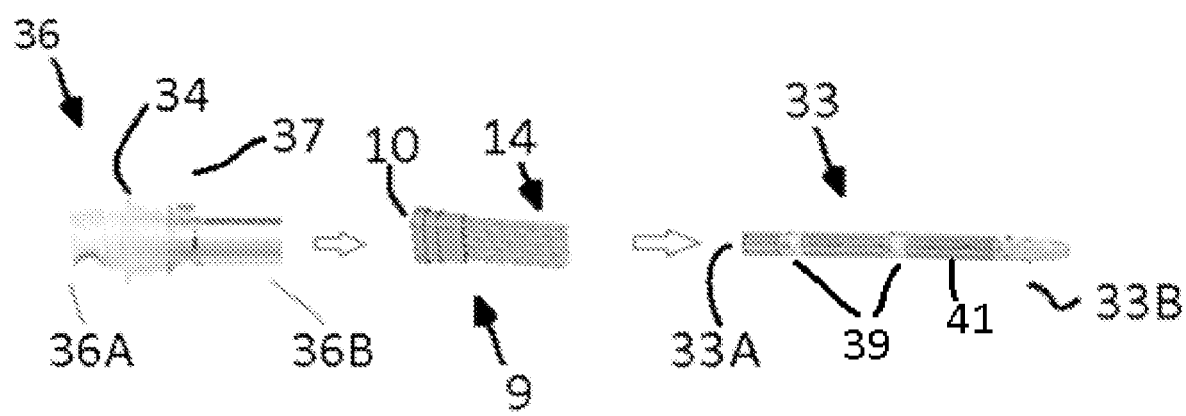
FIG. 16 is a side view of another embodiment of the present invention for venous use.

FIG. 16 is a side view of another embodiment of the present invention for venous use.

In another characteristic of this embodiment, the distal end 36B is disconnected from the holder 10, the plurality of ducts 14 is disconnected from the proximal portion 33A. In another characteristic of this embodiment, the internal connection 33 is disengaged from the middle part 9 which is disconnected from the external connection 36. In another characteristic of this embodiment, the internal connection 33 is longer and adapted for insertion into the conventional trocar 53. In another characteristic of this embodiment, the internal connection 33 is adapted to be positioned within the patients' circulatory system 26 B, as for example, the vena cava, but is not limited to them. In another characteristic of this embodiment, the markings 39 serve as a measure for how much of the internal connection 33 enters the patients' circulatory system 26B. In another characteristic of this embodiment, the invention comprises means for maintaining open the passage of blood, the spring 41 keeps the blood passageways 3 always open for the blood flow.

Figure 17:
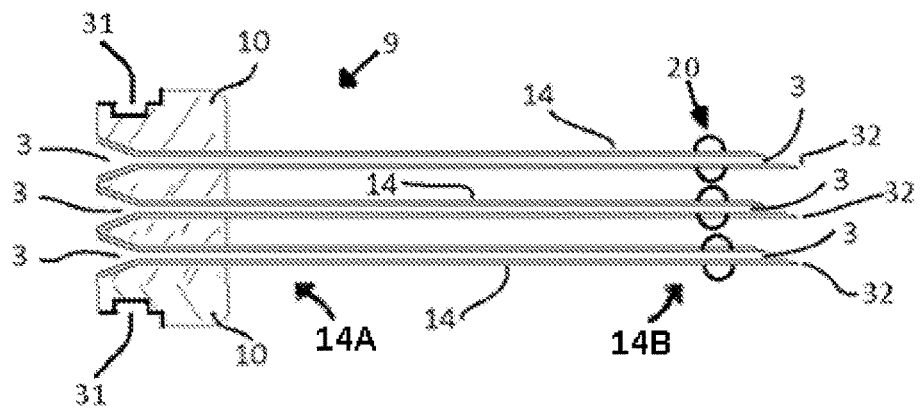
FIG. 17 is a sectional view of the middle part 9 adapted to perforate and transfix the tissue 25, according to another embodiment of the invention.

FIG. 17 is a sectional view of the middle part 9 adapted to perforate and transfix the tissue 25, according to another embodiment of the invention.

In another characteristic of this embodiment, the embodiment provides three blood passageways 3 through the tissue 25 to the surgical site 26. In another characteristic of this embodiment, the middle part 9 is the trocar set 42 including: the holder 10, and three plurality of ducts 14 connected to the holder 10.

In another characteristic of this embodiment, this embodiment is adapted to cause minimal trauma to the tissue 25 in order to prevent scars.

In another characteristic of this embodiment, the plurality of ducts 14 are adapted to cause minimal trauma to the tissue 25, in order to prevent scars. The plurality of ducts 14 has an outer diameter which is adapted to prevent scar formation in the tissue 25. In another characteristic of this embodiment, the outer diameter is thin enough to cause minimal trauma to the tissue 25 in order to avoid scars. In another characteristic of this embodiment, the three ducts 14 have the distal sharp tip 32 to, easily, penetrate the tissue 25 and not cause scars. Another characteristic of this embodiment is that it does not need the mandrel 1 to puncture the tissue 25, the plurality of ducts 14 are inserted directly in the tissue 25. In another characteristic of this embodiment, the holder 10 includes a socket 31. In another characteristic of this embodiment, it has no mandrel 1.

In some embodiments, the invention includes the mandrel 1, including the handle 7 and the mandrel 1 including the plurality of piercing tips 2, connected to the handle 7, wherein the mandrel 1 detachably engages the trocar set 42 forming a single punch assembly. In some embodiments, the plurality of ducts 14 has no sharp tip 32. In another characteristic of this embodiment, the plurality of ducts 14 comprises a fastening system 47 in the cardiovascular tissue 25B. In another characteristic of this embodiment, the plurality of ducts 14 has a balloon 20 as the fastening system 47 to fix the plurality of ducts 14 in the cardiovascular tissue 25B.

Figure 18:
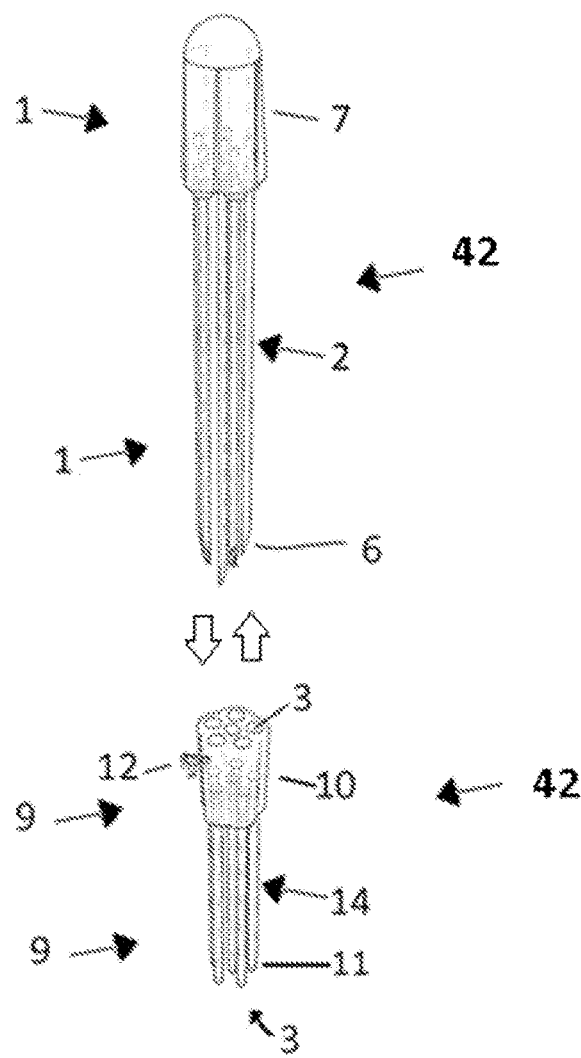
FIG. 18 is a perspective view of the mandrel 1 and the middle part 9 according to another embodiment of the invention.

FIG. 18 is a perspective view of the mandrel 1 and the middle part 9 according to another embodiment of the invention.

In another characteristic of this embodiment, there are six ducts 14 that provide six blood passageways 3 through the tissue 25 to the surgical site 26.

In another characteristic of this embodiment, the arrow shows the direction in which the mandrel 1 slides, longitudinally, to fit the middle part 9 perfectly to form single trocar set 42 insertion assembly. In another characteristic of this embodiment, each piercing tips 2 is solid and has the bezel 6 shaped tip that facilitates the tissue 25 insertion.

In another characteristic of this embodiment, after the insertion in tissue 25, the mandrel 1 is completely detachable from the middle part 9, and the middle part 9 remains in the tissue 25 during surgery, so that each duct 14 has the blood passageway 3 to the surgical site 26. In another characteristic of this embodiment, the faucet 12 controls the passage of liquid through the blood passageways 3 to the patients' circulatory system 26B, in accordance with another embodiment of the invention. In some embodiments the invention is disposable. In some embodiments the invention is permanent.

Figure 19:
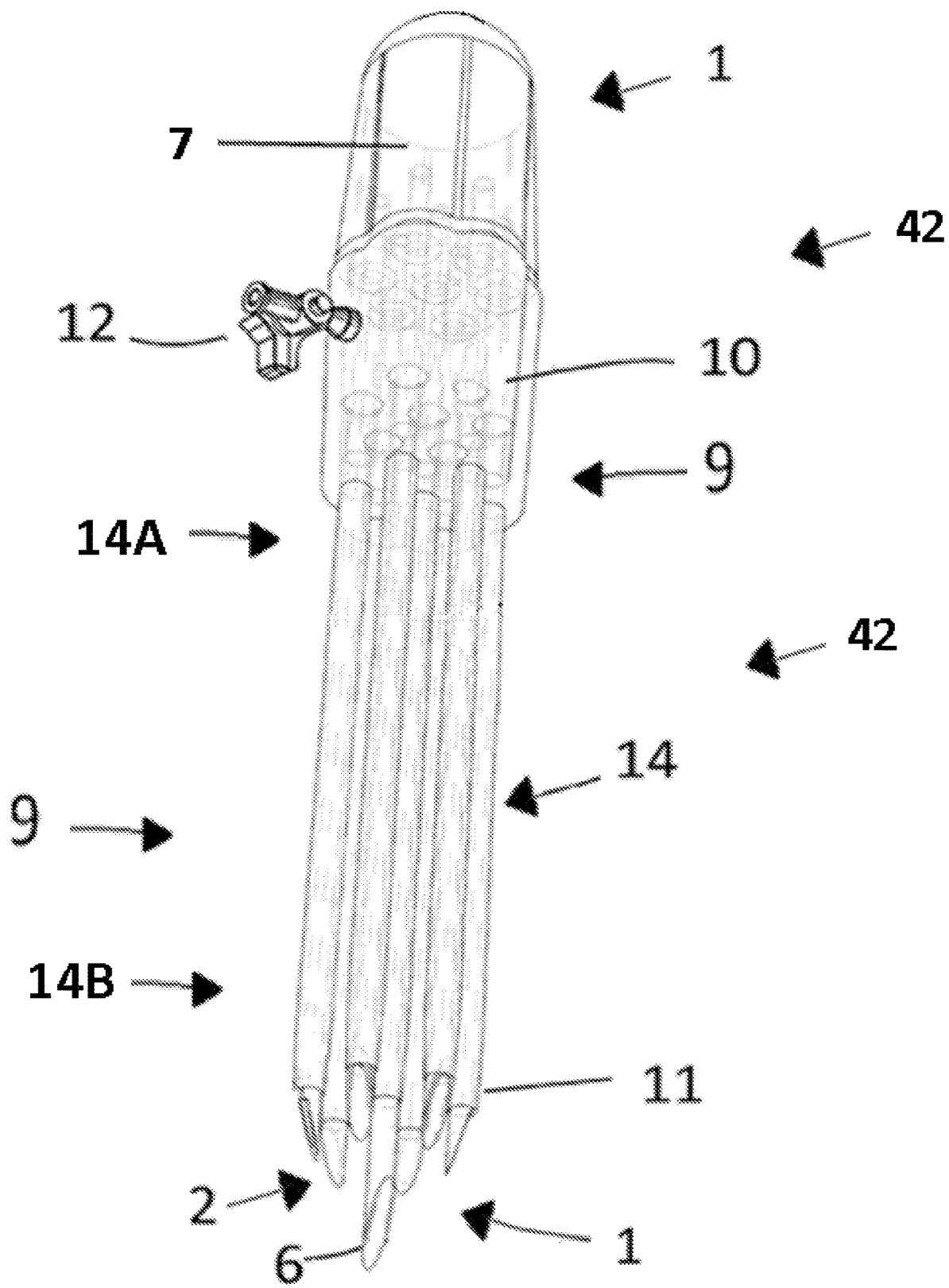
FIG. 19 is a perspective view of the trocar set 42, according to another embodiment of the invention.

FIG. 19 is a perspective view of the trocar set 42, according to another embodiment of the invention.

In another characteristic of this embodiment, the embodiment comprises the middle part 9 including the holder 10, and the middle part 9 including seven ducts 14 connected to the holder 10, the mandrel 1 including the handle 7; and the mandrel 1 including seven piercing tips 2 connected to the handle 7; wherein the mandrel 1 detachably engages the middle part 9 forming a single punch assembly. In another characteristic of this embodiment, it has no valve 13.

FIG. 20-21 are top views of some embodiments of the invention showing: some holder 10 shape, some positions of the blood passageways 3 in the holder 10, and some distributions of the blood passageways 3 in the holder 10.

FIG. 22 and FIG. 23 are top views of some embodiments of the invention adapted for the insertion of the intercostal space.

In another characteristic of this embodiment, the position of the blood passageways 3 is not limited to them, the number of the blood passageways is not limited to them. In some embodiments, the transversal shape of the blood passageways 3 is circular, in some embodiments, the transversal shape of the blood passageways 3 is elliptical; in some embodiments, the transversal shape of the blood passageways 3 is square, but the shapes of the blood passageways 3 are not limited to them. In another characteristic of this embodiment, the shape of the holder 10 is not limited to them.

FIG. 24 is a cross-sectional view of the mandrel 1, wherein two piercing tips 2 comprise a retractable 4 protection system, according to another embodiment invention, In another characteristic of this embodiment, the mandrel 1 has two piercing tips 2. In another characteristic of this embodiment, the retractable 4 slides longitudinally into a lumen 28 of the piercing tip 2. In another characteristic of this embodiment, a spring 5 is seen in two positions: shrunk position 5A, including the retractable 4 fully in the lumen 28 of the piercing tip 2, and in the extended position 5B, with the retractable 4 out of the lumen 28 of the piercing tip 2. Prior to puncturing the tissue 25, the retractable 4 is out of the lumen 28 of the piercing tip 2 externalizing out of the piercing tip 2 and the spring 5B is in an extended position. In the position 5B, the bezel 6 is protected by the retractable 4. In another characteristic of this embodiment, when the surgeon pushes the piercing tip 2 to insert the tissue 25, the retractable 4 is pushed by the tissue 25 and slides longitudinally into the piercing tip 2, and the retractable 4 compresses the spring 5 to position 5A. In another characteristic of this embodiment, when the tissue 25 has been transfixed, the spring 5 returns to the position 5B and, longitudinally, pushes the retractable 4 out of the lumen 28 of the piercing tip 2, in accordance with another embodiment of the invention. In some embodiments, the piercing tip 2 has the bezel 6 tip to insert the tissue 25. In another characteristic of this embodiment, the bezel 6 angulation is not limited to them. In another characteristic of this embodiment, the bezel 6 shape is not limited to them. In another characteristic of this embodiment, the bezel 6 shape of edging is not limited to them. In some embodiments, the piercing tip 2 is solid. In some embodiments, the piercing tip 2 has the lumen 28.

Figure 25:
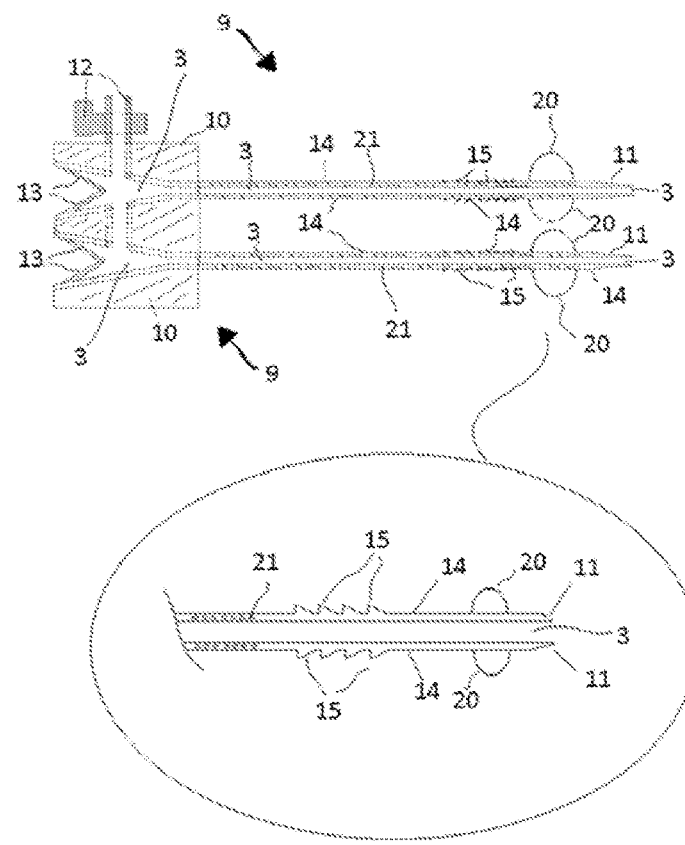
FIG. 25 is a cross-sectional view, wherein the plurality of ducts 14 comprise the fastening system 47 in the tissue 25, the figure in detail is an ampliation of the second end 14B end of the plurality of ducts 14, according to another embodiment of the invention.

FIG. 25 is a cross-sectional view, wherein the plurality of ducts 14 comprises the fastening system 47 in the tissue 25. The figure in detail is an ampliation of the second end 14B of the plurality of ducts 14, according to another embodiment of the invention.

In another characteristic of this embodiment, the middle part 9 includes two plurality of ducts 14. They are examples of the fastening systems 47: the grooves 15, the balloon 20, but it is not limited to them. In another characteristic of this embodiment, the grooves 15 comprise the fastening system 47 and assist in fixing the middle part 9 in the tissue 25, preventing the plurality of ducts 14, when punched in the tissue 25, to slide longitudinally in the tissue 25 during surgery. In another characteristic of this embodiment, the balloon 20 comprises the fastening system 47, the balloon 20 passes deflated through the tissue 25 and it is inflated after the plurality of ducts 14 transfixes the tissue 25. The balloons 20 are inflated by a pipe that passes along the duct 14 but is not limited to that.

In another characteristic of this embodiment, the invention comprises means for maintaining open the passage of blood through the blood passageways 3. In another characteristic of this embodiment, the plurality of ducts 14 comprises a coil 21, which keeps open the blood passageways 3 of the plurality of ducts 14. If the plurality of ducts 14 is flexed or folded, the coil 21 maintains pervious the blood passageways 3. In another characteristic of this embodiment, the dilator 11 is part of the plurality of ducts 14, it is a tapering area thereof, and serves to dilate the insertion hole made by the piercing tip 2. In another characteristic of this embodiment, the faucet 12 may be opened or closed to provide transfixions 44 through the blood passageways 3 of liquid or blood into the surgical site 26. In another characteristic of this embodiment, the valve 13 prevents liquids from returning from the blood passageways 3, out of the middle part 9, in accordance with another embodiment of the invention.

Figure 26:
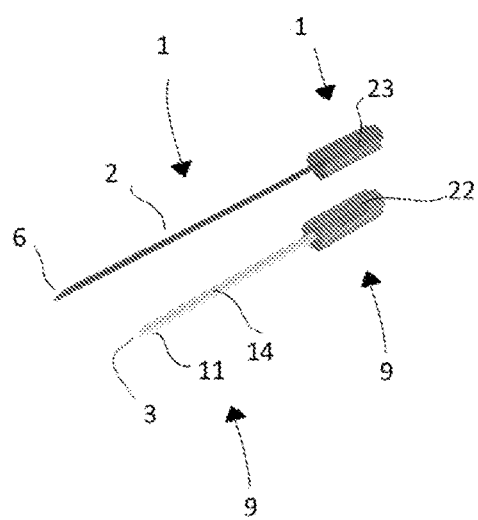
FIG. 26 is a perspective view of another embodiment of the invention, the invention is modular, including the module 23 and the block 22.

FIG. 26 is a perspective view of another embodiment of the invention, the invention is modular, including the module 23 and a block 22.

In another characteristic of this embodiment, the invention includes a module 23, the module 23 includes six sides.

In another characteristic of this embodiment, the module 23 has male-female connections to connect to another modules 23, to form the handle 7; the engagement is longitudinally slidable. Also, in another characteristic of this embodiment, the invention including the block 22 and the block 22 includes six sides. In another characteristic of this embodiment, the block 22 has male-female connections to connect to another blocks 22 to form the holder 10. In another characteristic of this embodiment, the engagement is longitudinally slidable. In another characteristic of this embodiment, the mandrel 1 is disengaged from the middle part 9, in accordance with another embodiment of the invention. In some embodiments, the handle 7 will be formed by the connection of at least two modules 23, and the holder 10 will be formed by the connection of at least two blocks 22.

Figure 27:
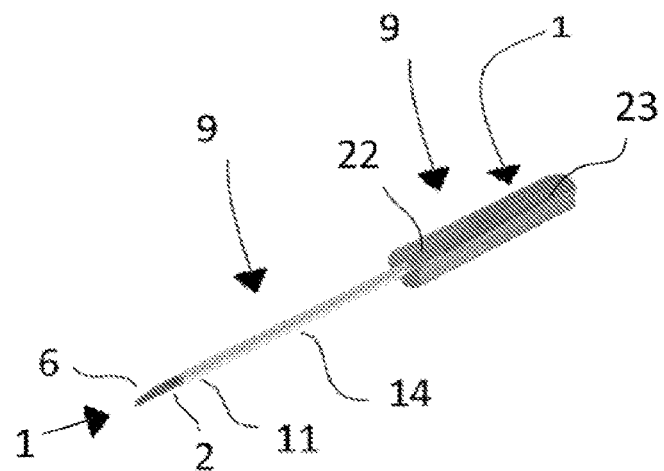
FIG. 27 is a perspective view of another embodiment of the invention, the invention is modular, the mandrel 1 is engaged in the middle part 9.

FIG. 27 is a perspective view of another embodiment of the invention, the invention is modular, the mandrel 1 is engaged in the middle part 9.

In another characteristic of this embodiment, the engagement is longitudinally slidable by the six sides. In another characteristic of this embodiment, the invention is modular and includes the module 23 and the block 22, the mandrel 1 is perfectly engaged in the middle part 9, forming a single punch assembly. In another characteristic of this embodiment, the module 23 connects perfectly to the block 22, the module 23 is made to connect another module 23. In another characteristic of this embodiment, the block 22 is made to connect another block 22, in accordance with another embodiment of the invention.

Figure 28:
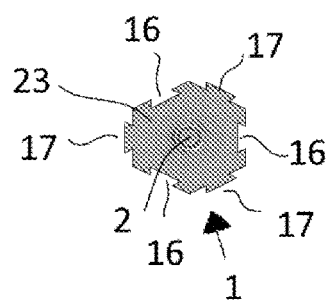
FIG. 28 is a top view of the module 23 according to another embodiment of the invention.

FIG. 28 is a top view of the module 23 according to another embodiment of the invention.

In another characteristic of this embodiment, the module 23 includes six sides: three sides including a female-link 16, and another three sides including a male-link 17.

In another characteristic of this embodiment, each the male-link 17 is shaped to engage the female-link 16 of another module 23. In another characteristic of this embodiment, the engagement is longitudinally slidable, the female-link 16 is constructed to fit longitudinally slidable in the male-link 17 of another module 23, the male-link 17 is constructed to fit longitudinally slidable in the female-link 16 of another module 23, in accordance with another embodiment of the invention.

Figure 29:
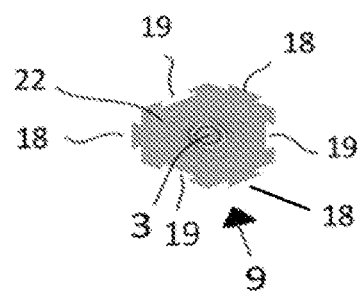
FIG. 29 is a top view of another embodiment of the block 22, according to another embodiment of the invention.

FIG. 29 is a top view of other embodiments of the block 22, according to other embodiments of the invention.

In another characteristic of this embodiment, the block 22 includes six sides: three sides including a female-connectors 19, three sides including a male-connectors 18.

In another characteristic of this embodiment, each male-connector 18 is shaped to engage the female-connectors 19 of another block 22. In another characteristic of this embodiment, the engagement is longitudinally slidable, the male-connector 18 is constructed to fit, longitudinally slidable, in the female-connector 19 of another block 22, the female-connector 19 is constructed to fit, longitudinally slidable, in the male-connector 18 of another modular block 22, in accordance with another embodiment of the invention.

Figure 30:
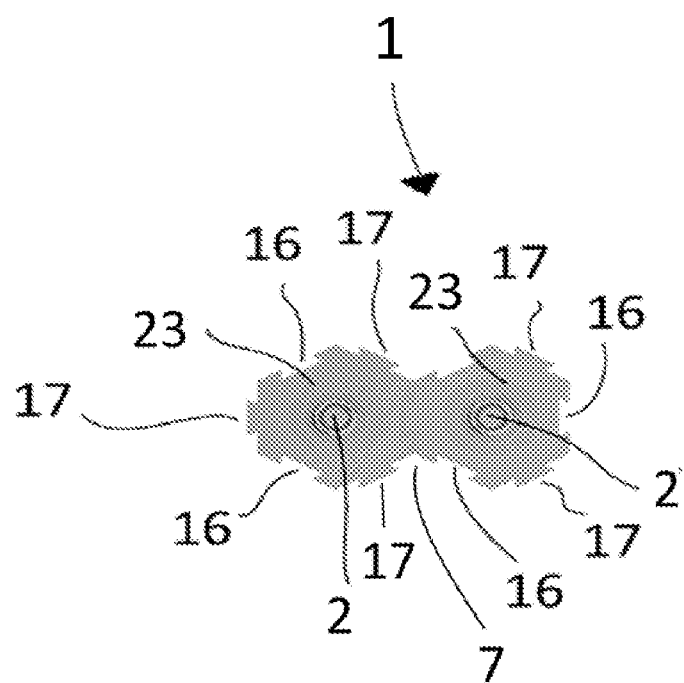
FIG. 30 is a top view of another embodiment of the invention including two connected modules 23.

FIG. 30 is a top view of two connected modules 23, according to another embodiment of the invention.

In another characteristic of this embodiment, the handle 7 is modular and formed by the joint of two or more modules 23, engaged in one another in a longitudinal sliding manner by male-female connector. In another characteristic of this embodiment, the female-link 16 is slidably engaged in the male-link 17 of another module 23, forming the handle 7, including two modules 23. In some embodiments, the handle 7 is formed by the connection of the plurality of modules 23, but the number of modules 23 is not limited to them. In another characteristic of this embodiment, the forms of engagement of the modules 23 are not limited to them, in accordance with another embodiment of the invention.

Figure 31:
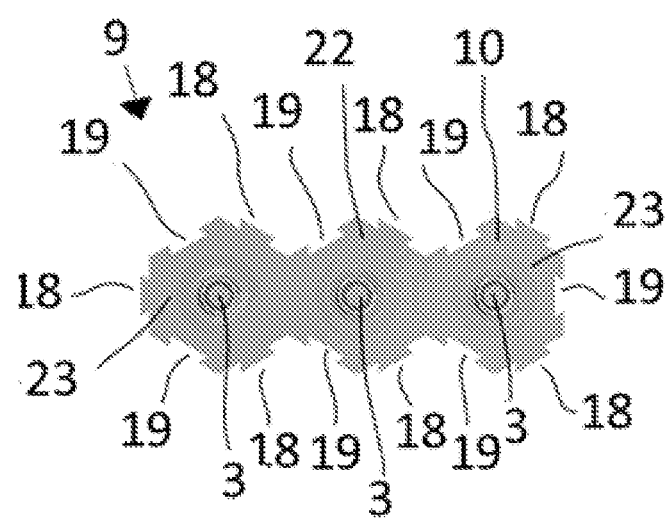
FIG. 31 is a top view of another embodiment of the invention, including three blocks 22.

FIG. 31 is a top view of another embodiment of the invention, including three blocks 22.

In another characteristic of this embodiment, the holder 10 is modular and formed by the connection of three blocks 22 connected in a longitudinal sliding manner. In another characteristic of this embodiment, the middle part 9 is made by the connection of three blocks 22.

Figure 32:
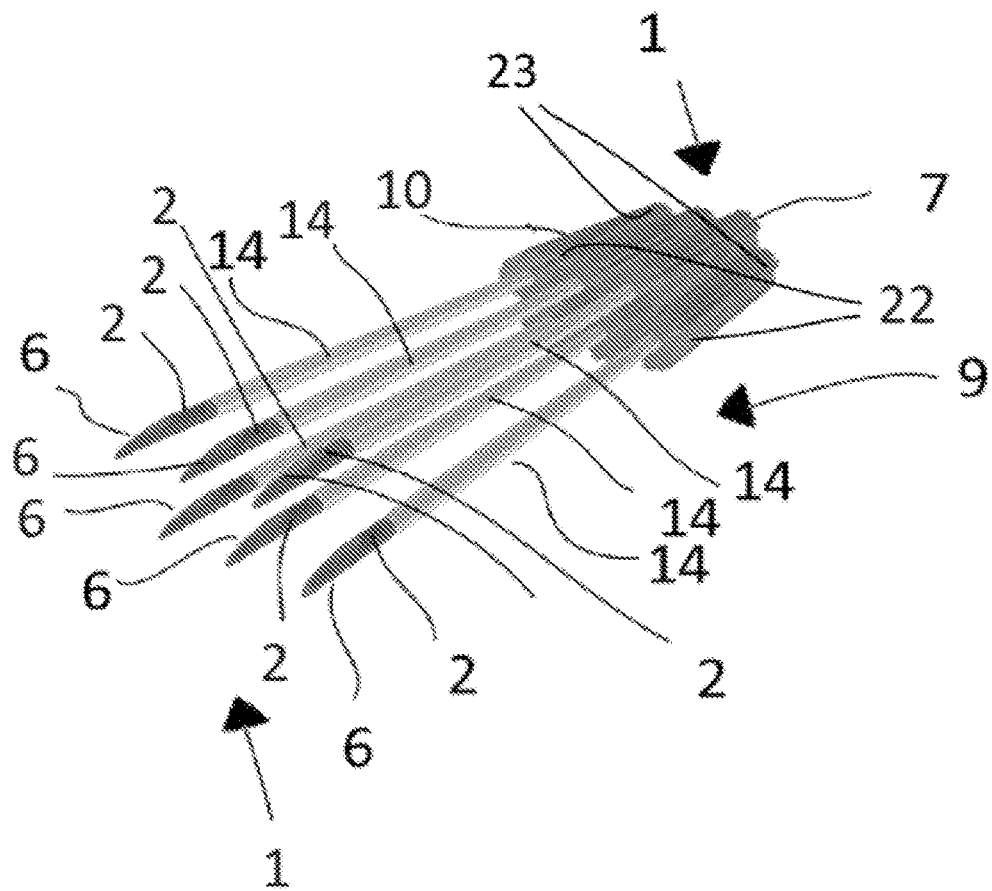
FIG. 32 is a perspective view of another embodiment of the invention, the six modules 23 are connected in a suitable way to insertion the intercostal space, it is made to accompanying the shape of the ribs in the chest.

FIG. 32 is a perspective view of another embodiment of the invention, the six modules 23 are connected in a suitable way to puncture the intercostal space, it is made to accompany the shape of the ribs in the chest.

In another characteristic of this embodiment, the trocar set 42 is modular and includes six connected modules 23 and six connected blocks 22. In another characteristic of this embodiment, the mandrel 1 is perfectly engaged in the middle part 9, the modules 23 engages perfectly into the blocks 22. In another characteristic of this embodiment, the mandrel 1 is formed by six modules 23 connected modularly and sliding longitudinally, the middle part 9 is formed by six blocks 22 connected longitudinally and slidably engaged. In another characteristic of this embodiment, the mandrel 1 detachably engages the middle part 9, forming a single punch assembly, in accordance with another embodiment of the invention.

Figure 33:
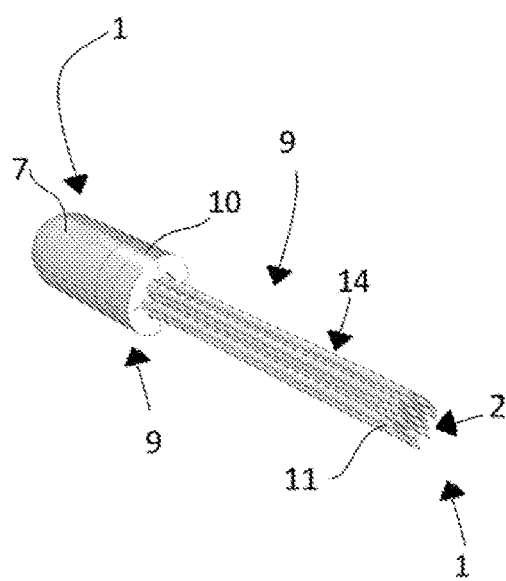
FIG. 33 is a perspective view of another embodiment of the invention in a modular configuration for providing seven blood passageways 3 through tissue 25 to the surgical site 26.

FIG. 33 is a perspective view of another embodiment of the invention in a modular configuration for providing seven blood passageways 3 through tissue 25 to the surgical site 26.

In another characteristic of this embodiment, the mandrel 1 is modular and perfectly engaged into the modular middle part 9, forming a single punch assembly. In another characteristic of this embodiment, the mandrel 1 is modular and includes the handle 7, which is connected to seven piercing tips 2, and the middle part 9 is modular and includes the holder, which 10 connected to seven ducts 14. In another characteristic of this embodiment, the mandrel 1 is adapted to be completely detachable from the middle part 9, by sliding the mandrel 1 longitudinally relative to the middle part 9. In another characteristic of this embodiment, the handle 7 is modular and has seven female-links 16 (not seen) connected in seven modules 23. In another characteristic of this embodiment, each module 23 has the piercing tip 2. In another characteristic of this embodiment, the middle part 9 is modular and has the holder 10 including seven female-connectors 19 (not seen), seven blocks 22 are embedded in the female-connectors 19. In another characteristic of this embodiment, block 22 has the plurality of ducts 14, according to another embodiment of the invention.

Figure 34:
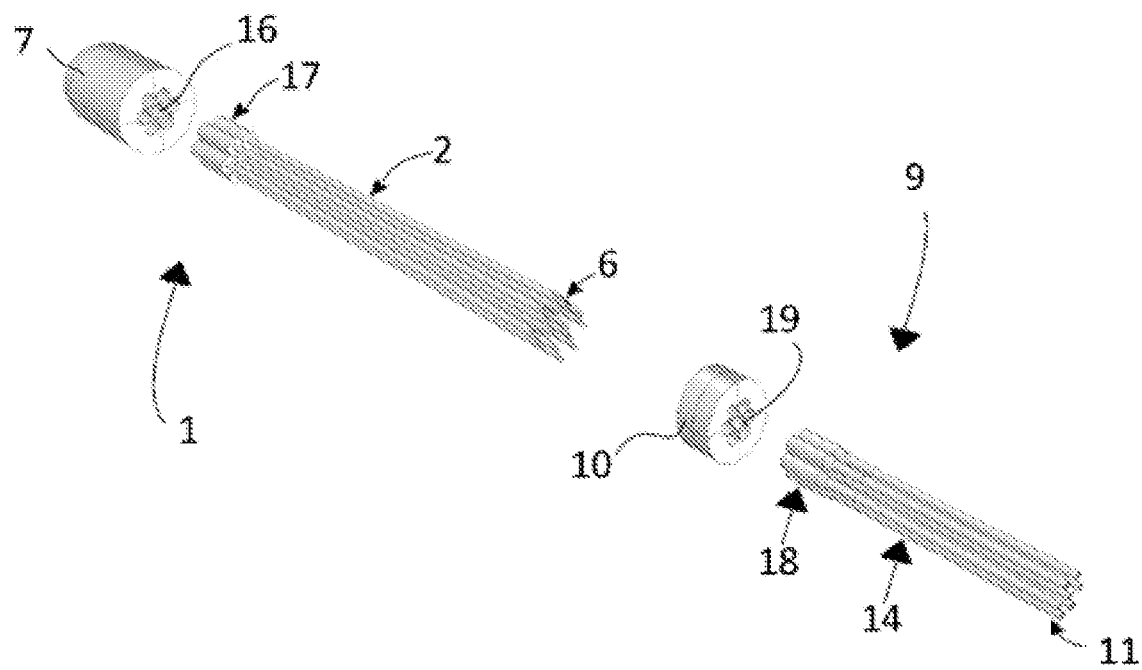
FIG. 34 is a perspective view of another embodiment of the invention, the modular parts are disconnected.

FIG. 34 is a perspective view of another embodiment of the invention, the modular parts are disconnected.

In another characteristic of this embodiment, the embodiment contains: the handle 7, including seven female-links 16, and the holder 10, including seven female-connectors 19. In another characteristic of this embodiment, male-link 17 connects the female-link 16 in longitudinal sliding movement. In another characteristic of this embodiment, the surgeon chooses the number of piercing tips 2 that will be engaged in the handle 7. In another characteristic of this embodiment, the middle part 9 has the holder 10 including seven female-connectors 19, each one of the ducts 14 has the male-connector 18 that connects to the female-connector 19. In another characteristic of this embodiment, the surgeon chooses the number of ducts 14 to fit into the holder 10, in accordance with another embodiment of the invention. In some embodiments, the shape, the size, and the types of the modular parts are different.

Figure 35:
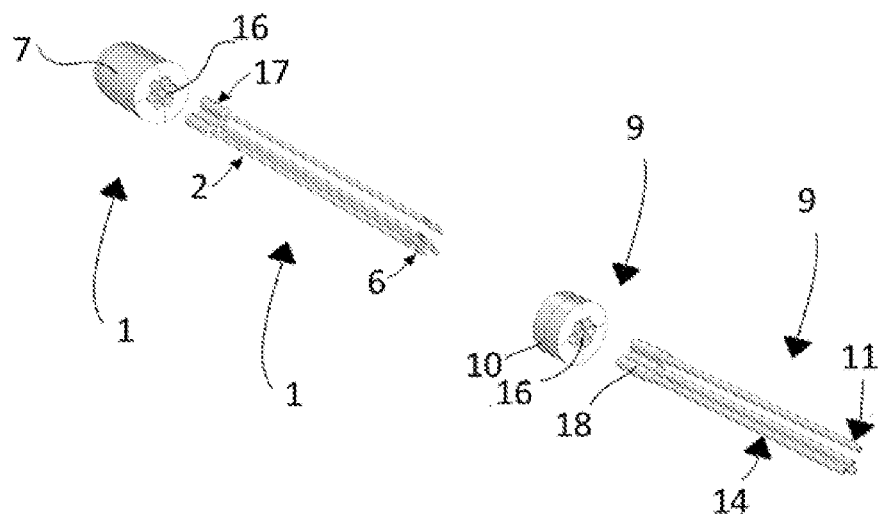
FIG. 35 is a perspective view of another embodiment of the invention, including: seven female-links 16 to connect four male-links 17 and seven female-connectors 19 to connect four male-connectors 18.

FIG. 35 is a perspective view of another embodiment of the invention. The embodiment includes: seven female-links 16 to connect four male-links 17 and seven female-connectors 19 to connect four male-connectors 18.

In another characteristic of this embodiment, the surgeon chooses which of the seven female-links 16 connect the four male-links 17 and which of the seven female-connectors 19 connects the four male-connectors 18. In another characteristic of this embodiment, the modular parts are disconnected. In another characteristic of this embodiment, the mandrel 1 has the handle 7 including seven female-links 16, four of the male-links 17 of the piercing tips 2 are aligned for connect in the female-links 16 in a longitudinal sliding movement. In another characteristic of this embodiment, the middle part 9 has the holder 10, including seven female-connectors 19, four of the male-connectors 18 of the ducts 14 are aligned to fit in the female-connectors 19 in a longitudinal sliding movement, in accordance with another embodiment of the invention.

Figure 36:
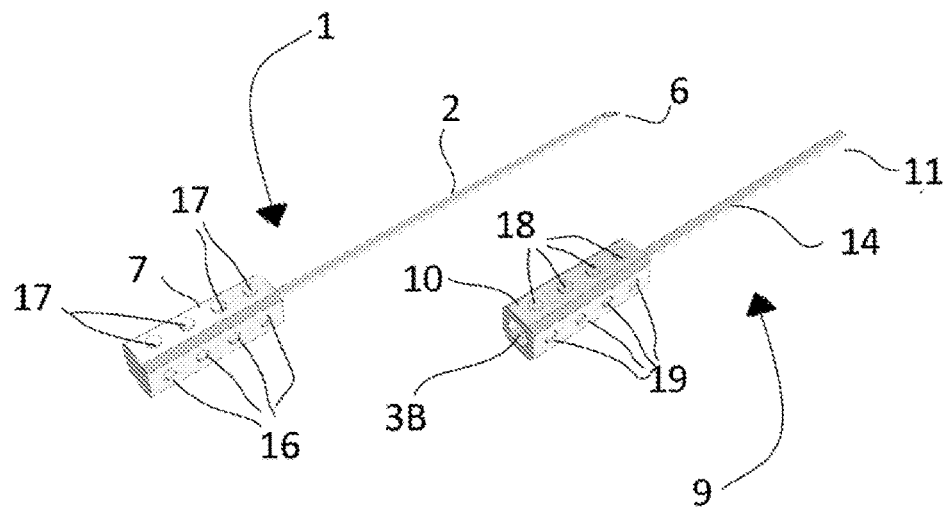
FIG. 36 is a perspective view of another embodiment of the invention in a modular configuration.

FIG. 36 is a perspective view of another embodiment of the invention in a modular configuration.

In another characteristic of this embodiment, the handle 7 has four sides, two of them including male-links 17 and another two including female-links 16. In another characteristic of this embodiment, the holder 10 also has four sides, two of them including male-connectors 18 and another two including female-connectors 19. In another characteristic of this embodiment, the modular parts connect substantially similar to the "Lego Toy" male-to-female connectors.

Figure 37:
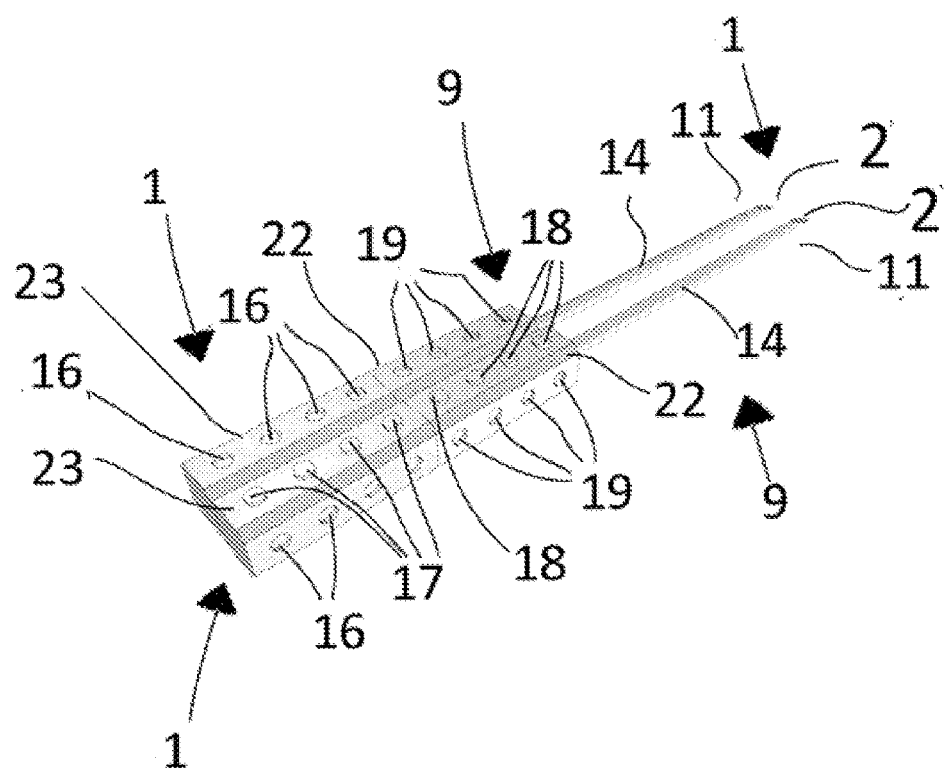
FIG. 37 is a perspective view of another embodiment of the invention, in a modular configuration including four connection sides.

FIG. 37 is a perspective view of another embodiment of the invention, in a modular configuration including four connection sides.

In another characteristic of this embodiment, the mandrel 1 has the handle 7 modular formed by the connection of two modules 23 and the middle part 9 has the holder 10 modular formed by the connecting of two blocks 22. In another characteristic of this embodiment, the mandrel 1 is perfectly engaged in the middle part 9, the mandrel 1 has the handle 7 modular formed by the connection of two modules 23, one module 23 is connected side by side to another module 23, four male-links 17 of the module 23 are connected to four female-links 16 of another module 23. In another characteristic of this embodiment, module 23 has four connection sides, each side has four connectors, two of them including four male-links 17 another two sides including four female-links 16. In another characteristic of this embodiment, module 23 includes the piercing tip 2, in accordance with another embodiment of the invention.

In another characteristic of this embodiment, the middle part 9 has the holder 10 modular formed by the connection of two blocks 22, which are connected side by side to another block 22. In another characteristic of this embodiment, block 22 has four connection sides. In another characteristic of this embodiment, four male-connectors 18 of one block 22 are connected to four female-connectors 19 of another block 22. In a cross-section view, each of the block 22 has four sides, each side including four connectors, two of them including four male-connectors 18 and another two sides including four female-connectors 19. In another characteristic of this embodiment, block 22 has the ducts 14. In another characteristic of this embodiment, the mandrel 1, detachably engages the middle part 9, forming a single punch assembly, according to another embodiment of the invention.

Figure 38:
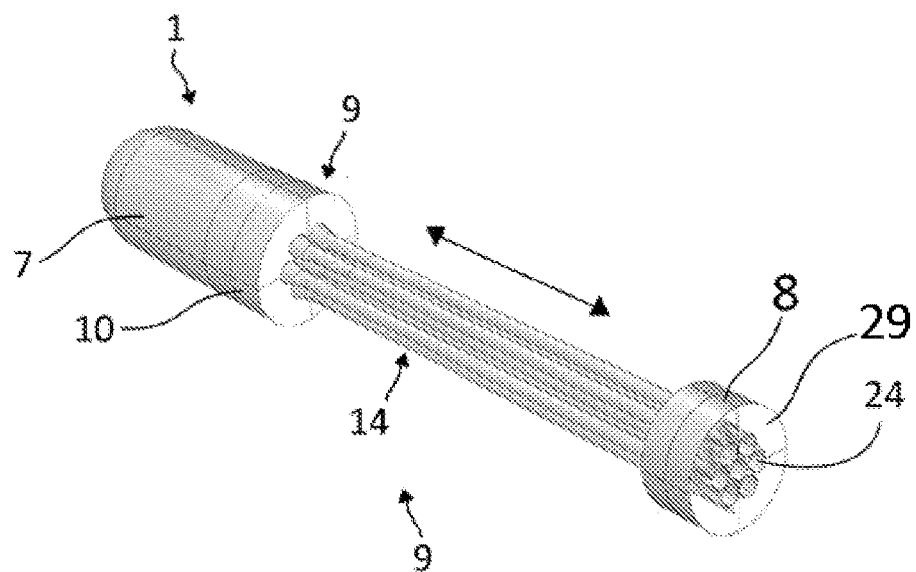
FIG. 38 is a perspective view of another embodiment of the invention, including the protector guide 8.

FIG. 38 is a perspective view of another embodiment of the invention, including a protector guide 8.

In another characteristic of this embodiment, the protector guide 8 is on the plurality of ducts 14. In another characteristic of this embodiment, the protector guide 8 is movable over the plurality of ducts 14 and is adapted to be moved from the holder 10 to the second end 14B of the plurality of ducts 14. When positioned in the second end 14B of the plurality of ducts 14, it protects the dilator 11 and protects the bezel 6 of the piercing tip 2. In another characteristic of this embodiment, there is a beater 27 at the second end 14B of the plurality of ducts 14, which prevents the protector guide 8 of coming out of the plurality of ducts 14. In another characteristic of this embodiment, the protector guide 8 has a protective function, so the bezel 6 does not injure something inadvertently and has a hole 24 to correctly direct the penetration of the plurality of ducts 14 into the tissue 25. In another characteristic of this embodiment, the two-headed arrow indicates the movement of the protector guide 8 on the plurality of ducts 14, according to another embodiment of the invention. In another characteristic of this embodiment, the protector guide 8 has the hole 24 for the passage of the plurality of ducts 14.

FIG. 39, FIG. 40, FIG. 41, FIG. 42, and FIG. 43 are cross-sectional views of some embodiments of the invention, including the method of providing a plurality of blood passageways 3 through tissue 25 to the surgical site 26. In another characteristic of this embodiment, the method of providing the plurality of blood passageways 3 through tissue 25 to the surgical site 26, includes: (a) transfixing the plurality of ducts 14 in the tissue 25 to the surgical site 26; (b) using, at least, one blood passageway 3 to pass blood of an extracorporeal circulation; and (c) removing the ducts 14 of the tissue 25, is provided. In another characteristic of this embodiment, the methods further include: (d) detach the mandrel 1 within the middle part 9; (e) connecting the external connection 36 to at least one duct 14; (f) inserting, at least, one of the plurality of pipes 51 in the patients' circulation system 26B; (g) inserting, at least, one duct 14 in the patients' circulation system 26B. In another characteristic of this embodiment, the acts or operations of the methods or processes can be performed in any suitable sequence and are not necessarily limited to any disclosed sequence.

A method for extracorporeal blood circulation includes: inserting a plurality of ducts 14 of a cardiovascular cannula 50 into a surgical site 26 through a plurality of transfixions in the tissue, connecting the cardiovascular cannula 50 to a patients' circulatory system, connecting the cardiovascular cannula 50 to an extracorporeal circulation apparatus 35, inserting a second cardiovascular cannula 50 into a surgical site 26, connecting the second cardiovascular cannula 50 to a patients' circulatory system, connecting the second cardiovascular cannula 50 to an extracorporeal circulation apparatus 35, perform an extracorporeal circulation.

The method further includes, connecting an internal connection 33 to the cardiovascular cannula 50.

The method further includes, removing the cardiovascular cannula 50 of a patients' circulatory system and removing the second cardiovascular cannula 50 of a patients' circulatory system, is provided.

FIG. 39, FIG. 40, FIG. 41, FIG. 42, and FIG. 43 are described in more detail below, according to some embodiments of the invention.

Figure 39:
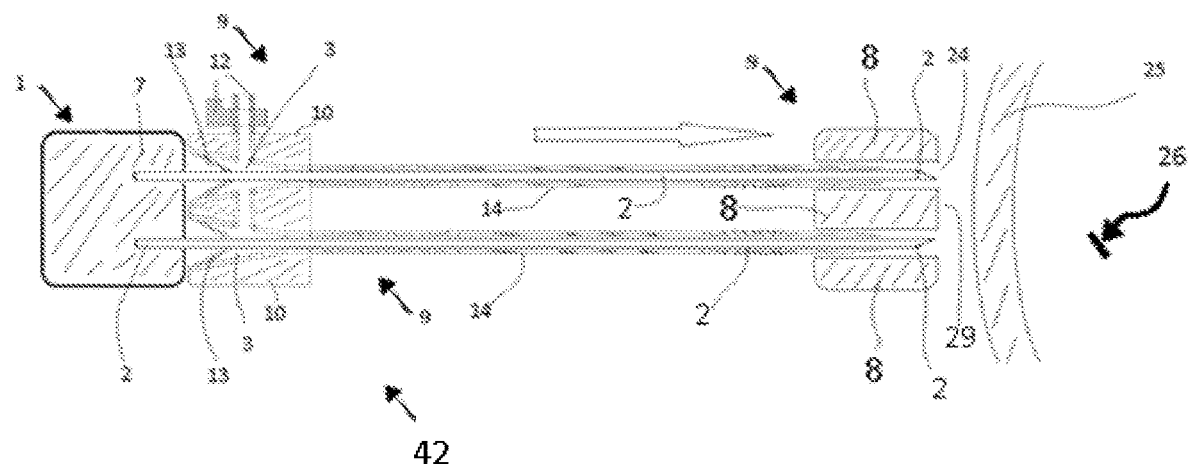

FIG. 39 is a cross-sectional view of the protector guide 8, positioned at the second end 14B of the plurality of ducts 14, according to another embodiment of the invention, In another characteristic of this embodiment, the method of punching the trocar set 42 includes two ducts 14 in the tissue 25 to insert in the surgical site 26

In another characteristic of this embodiment, the bezel 6 and the dilator 11 are protected inside the hole 24. In another characteristic of this embodiment, the beater 27 prevents the protector guide 8 from coming out of the plurality of ducts 14. In another characteristic of this embodiment, the mandrel 1 and the middle part 9 form a single punch assembly to puncture the tissue 25, providing the plurality of blood passageways 3 through the tissue 25 to the surgical site 26, according to another embodiment of the invention.

In another characteristic of this embodiment, the protector guide 8 has the hole 24 through which the plurality of ducts 14 pass. In another characteristic of this embodiment, the protector guide 8 has two functions: driving the piercing tips 2 during the tissue 25 insertion and protecting the bezel 6 so as not to, inadvertently, injure something. Punching the trocar set 42 including two ducts 14 in the tissue 25 to perforate 44 the surgical site 26. In another characteristic of this embodiment, for the insertion of the trocar set 42 in the tissue 25, the surgeon abuts a face 29 of the protector guide 8 to the tissue 25 and pushes the trocar set 42 against the tissue 25. In another characteristic of this embodiment, the holes 24 of the protector guide 8 drive the piercing tips 2 that perforate the tissue 25 in a driveway, according to another embodiment of the invention.

Figure 40:
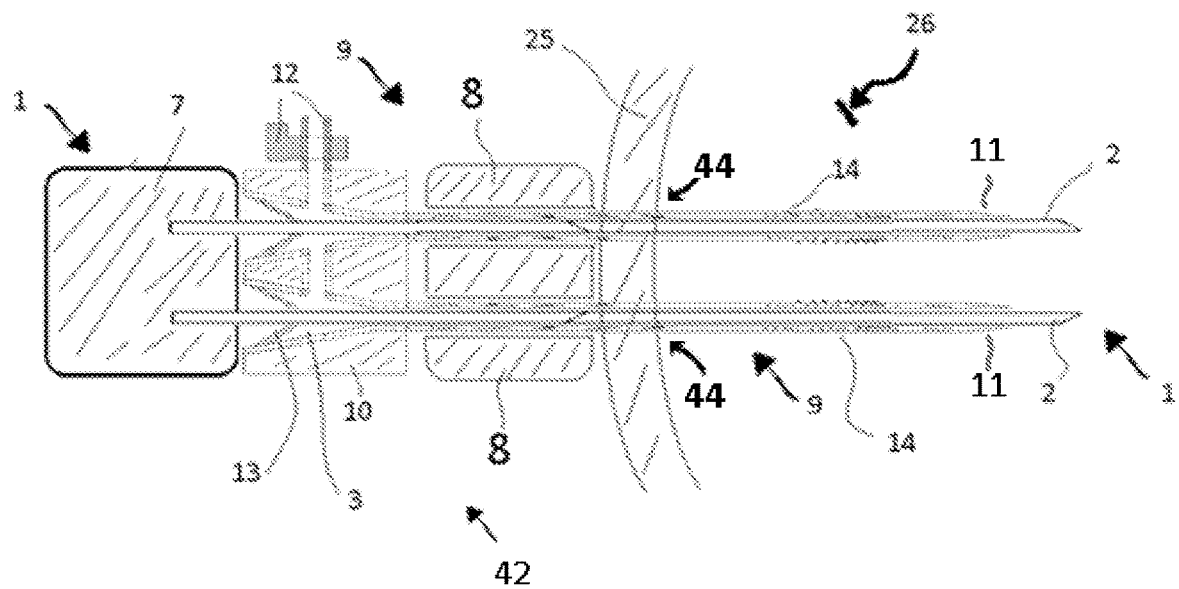
FIG. 40 is a cross-sectional view of another embodiment of the invention, including the method of punching the trocar set 42 including two ducts 14 in the tissue 25 to insert in the surgical site 26, according to another embodiment of the invention.

FIG. 40 is a cross-sectional view of other embodiments of the invention, including the method of punching the trocar set 42 including two ducts 14 in the tissue 25 to insert in the surgical site 26, according to another embodiment of the invention.

In another characteristic of this embodiment, the mandrel 1 and the middle part 9 form a single punch assembly which has been inserted in the tissue 25. In another characteristic of this embodiment, the plurality of ducts 14 passes through the protector guide 8 through the hole 24, traverses the tissue 25 and reaches the surgical site 26. In another characteristic of this embodiment, the dilator 11 dilates the hole made by the piercing tip 2, allowing the passage of the plurality of ducts 14. In another characteristic of this embodiment, the hole 24 is positioned in the proximal end 36A of the plurality of ducts 14 near the holder 10. In another characteristic of this embodiment, the mandrel 1 has not yet been detached from the middle part 9, the piercing tip 2 is inside the plurality of ducts 14 and the bezel 6 is inside the surgical site 26. In another characteristic of this embodiment, to use the blood passageways, the surgeon detaches the mandrel 1 within the middle part 9 by longitudinal traction.

Figure 41:
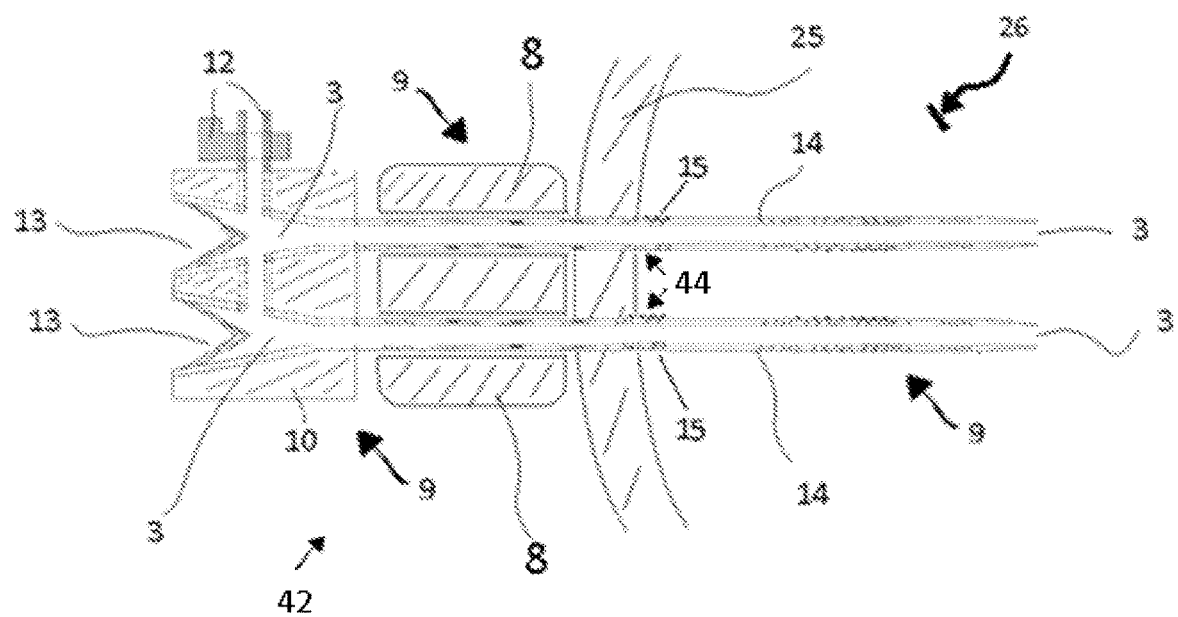
FIG. 41 is a cross-sectional view of middle part 9 providing two blood passageways through the tissue 25, according to another embodiment of the invention.

FIG. 41 is a cross-sectional view of middle part 9, providing two blood passageways through the tissue 25, according to another embodiment of the invention, In another characteristic of this embodiment, the mandrel 1 has been detached from the middle part 9 by longitudinal traction. In another characteristic of this embodiment, the middle part 9 is positioned in the tissue 25 and is now the blood passageway 3 through tissue 25 of the video instrument to the surgical site 26. In another characteristic of this embodiment, the plurality of ducts 14 of the middle part 9 is transfixing the tissue 25. In another characteristic of this embodiment, the ducts 14 were inserted into the surgical site 26 through two transfixions 44 in the tissue 25. In another characteristic of this embodiment, the valves 13 prevent gas or liquid from flowing out of the surgical site 26. In another characteristic of this embodiment, the faucet 12 allows the inflation of gas or liquid into the surgical site 26. The fastening system 47 includes grooves 15, secures the plurality of ducts 14 in the tissue 25 and prevents the plurality of ducts 14 from sliding on the tissue 25. In another characteristic of this embodiment, the blood passageways 3 allow the installation of the extracorporeal blood circulation without scarring. In another characteristic of this embodiment, removing the plurality of ducts 14 from the tissue 25, after the surgery, the trocar set 42 is removed from the tissue 25 by longitudinal traction, according to another embodiment of the invention.

Figure 42:
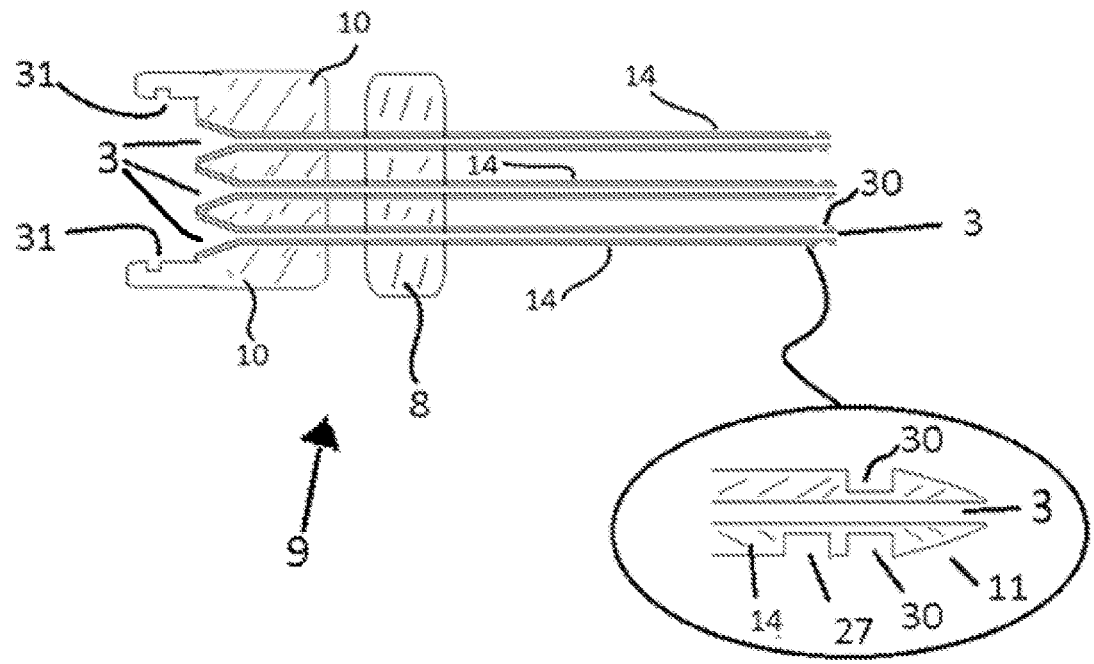
FIG. 42 is a cross-sectional view of the middle part 9 that is adapted to connect to at least one internal connection 33 in the surgical site 26 and adapted to connect to the external connection 36 outside the tissue 25, according to another embodiment of the invention.

FIG. 42 is a cross-sectional view of the middle part 9 that is adapted to connect to at least one internal connection 33 in the surgical site 26 and is adapted to connect to the external connection 36 outside the tissue 25, according to another embodiment of the invention.

Wherein, at least, one of the plurality of ducts 14 is adapted to connect to the internal connection 33 in the surgical site 26.

In the detail, there is a drawing showing the second end 14B of the plurality of ducts 14, according to one embodiment of the invention. In another characteristic of this embodiment, the trocar set 42 provides three blood passageways through the tissue 25 into the surgical site 26. In another characteristic of this embodiment, the trocar set 42 assembly includes: the middle part 9 including the holder 10 and three plurality of ducts 14 connected to the holder 10. In another characteristic of this embodiment, the three plurality of ducts 14 are adapted to cause minimal trauma to the tissue 25 in order to prevent scarring, the plurality of ducts 14 are thin enough to cause minimal trauma to the tissue 25. Also, the three plurality of ducts 14 further include the sharp tip 32 distal to insert in the tissue 25, avoiding scarring the tissue 25. In another characteristic of this embodiment, the holder 10 includes the socket 31 to connect to the external connection 36. In another characteristic of this embodiment, the plurality of ducts 14 includes the beater 27 and the fitting 30, according to another embodiment of the invention.

In another characteristic of this embodiment, the holder 10 is adapted to connect to a surgical device 52. In another characteristic of this embodiment, at least one surgical device 52 may be connected to the socket 31, but it is not limited to them. In another characteristic of this embodiment, there are some surgical devices 52 that may be connected to the holder 10: the extracorporeal hose 35, a suction appliance, a cannula, a video camera, guide, introduction guide, a surgical instrument, a measurement instrument, an electronic appliance, a surgical robot, an adapter, a cable, a pneumatic appliance, but it is not limited to them. In some embodiments, a surgical device 52 is connected the middle part 9 in a detachable way. In some embodiments, the connection of the surgical device 52 to the holder 10 is in a sealant way. In some embodiments, the connection of the surgical device 52 to the holder 10 is in a non-sealant way. In some embodiments, the connection of the surgical device 52 to the holder 10 is in a removable way. In some embodiments, the connection of the surgical device 52 to the holder 10 is in a non-removable way, but it is not limited to them. In some embodiments, the connection of the surgical device 52 to the holder 10 is made by friction. In some embodiments, the connection of the surgical device 52 to the holder 10 is made by electrical connection. In some embodiments, the connection of the surgical device 52 to the holder 10 is made by mechanical connections, but the type of connection is not limited to them. In some embodiments, there is a mechanism in the middle part 9 for releasing or connecting the surgical device 52 in the holder 10, for example: a button or a lever, according to another embodiment of the invention.

In another characteristic of this embodiment, the plurality of ducts 14 are adapted to connect the internal connection 33 inside the surgical site 26. In some embodiments, the plurality of ducts 14 includes the beater 27, which both serves to prevent the protector guide 8 from slipping out of the plurality of ducts 14 and to connect the internal connection 33 in the surgical site 26 to the plurality of ducts 14. In some embodiments, the fitting 30 connects the internal connection 33 in the surgical site 26 to the plurality of ducts 14. In some examples, at least one of the plurality of ducts 14 is adapted to connect at least one internal connection 33 in the surgical site 26. In some embodiments, the connection of the internal connection 33 in the surgical site 26 to the plurality of ducts 14 is made by friction. In some embodiments, the connection of the internal connection 33 in the surgical site 26 to the plurality of ducts 14 is made by electrical connection, in some embodiments, the connection of the internal connection 33 in the surgical site 26 to the plurality of ducts 14 is made by mechanical connection, but the type of connection is not limited to them. In some embodiments, the internal connection 33 in the surgical site 26 that connects the second end 14B of the plurality of ducts 14 are: a hose, a cannula, an electronic appliance, a mechanical appliance, but it is not limited to them. In some embodiments, there is a mechanism in the middle part 9 for releasing or connecting the internal connection 33 in the surgical site 26 to the plurality of ducts 14, for example: a button or a lever. In some embodiments, the fixation is not limited to single plurality of ducts 14. In some embodiments, the internal connection 33 is connected to, at least, one of the plurality of ducts 14 in the surgical site 26 after the trocar set 42 is inserted in the tissue 25, according to another embodiment of the invention.

In another characteristic of this embodiment, after the surgery, the trocar set 42 is removed from the tissue 25, the surgeon pulls the middle part 9 out of the tissue 25, according to another embodiment of the invention.

Figure 43:
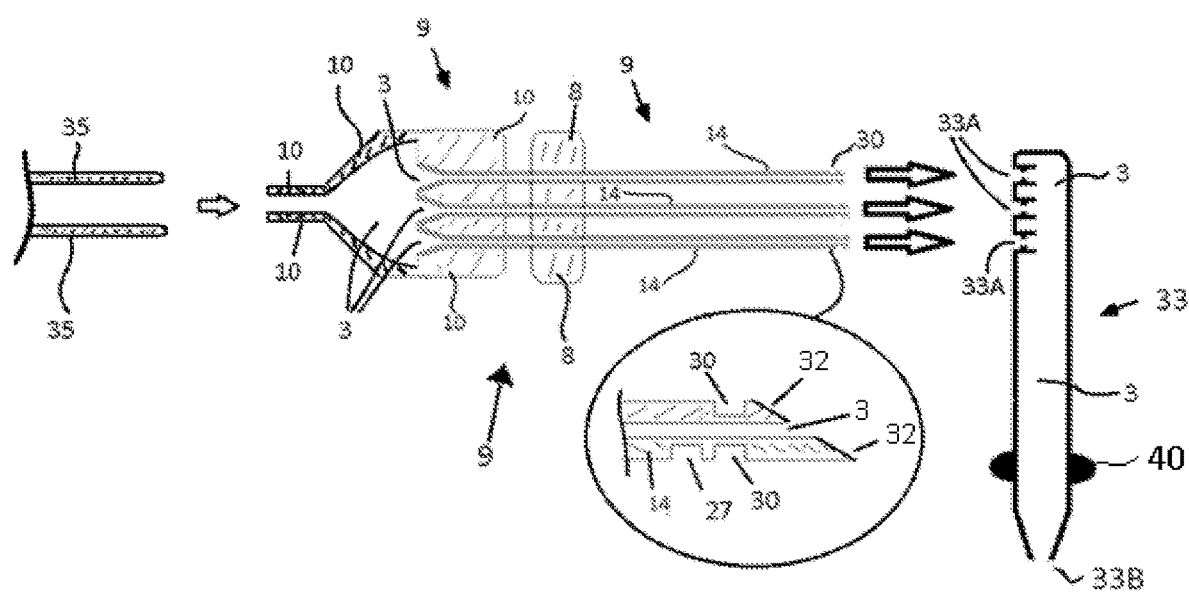
FIG. 43 is sectional view of the cardiovascular cannula 50 assembly for extracorporeal blood circulation by a plurality of transfixions 44 through the tissue 25 according to another embodiment of the invention.

FIG. 43 is sectional view of the cardiovascular cannula 50 assembly for extracorporeal blood circulation by a plurality of transfixions 44 through the tissue 25, according to another embodiment of the invention.

In another characteristic of this embodiment, the embodiment includes: the holder 10 to connect to the extracorporeal circulation apparatus 35 hose; the plurality of ducts 14 connected to the holder 10 to allow blood flow through the plurality of blood passageways 3 through the tissue 25; and the internal connection 33 for connecting the blood flow from the plurality of ducts 14 to the blood flow of the cardiovascular tissue 25B.

In another characteristic of this embodiment, the holder 10 is adapted to connect to the extracorporeal circulation apparatus 35 hose. In another characteristic of this embodiment, the guide 8 is adapted to slide over the plurality of ducts 14. In another characteristic of this embodiment, the beater 27 prevents the guidewire from exiting the ducts 14. In another characteristic of this embodiment, the beating 27 may be a flattening in the duct 14, the shape of the beater 27 is not limited to them. In another characteristic of this embodiment, the plurality of ducts 14 is adapted to transfix the tissue 25 and to connect the internal connection 33 into the surgical site 26. In another characteristic of this embodiment, the distal portion 33B of the internal connection 33 is configured to connect to the plurality of ducts 14. In another characteristic of this embodiment, the distal portion 33B is configured to be introduced into the patients' circulatory system 26B. In detail, the second end 14B of the plurality of ducts 14 with the sharp tip 32 is seen.

Figure 44:
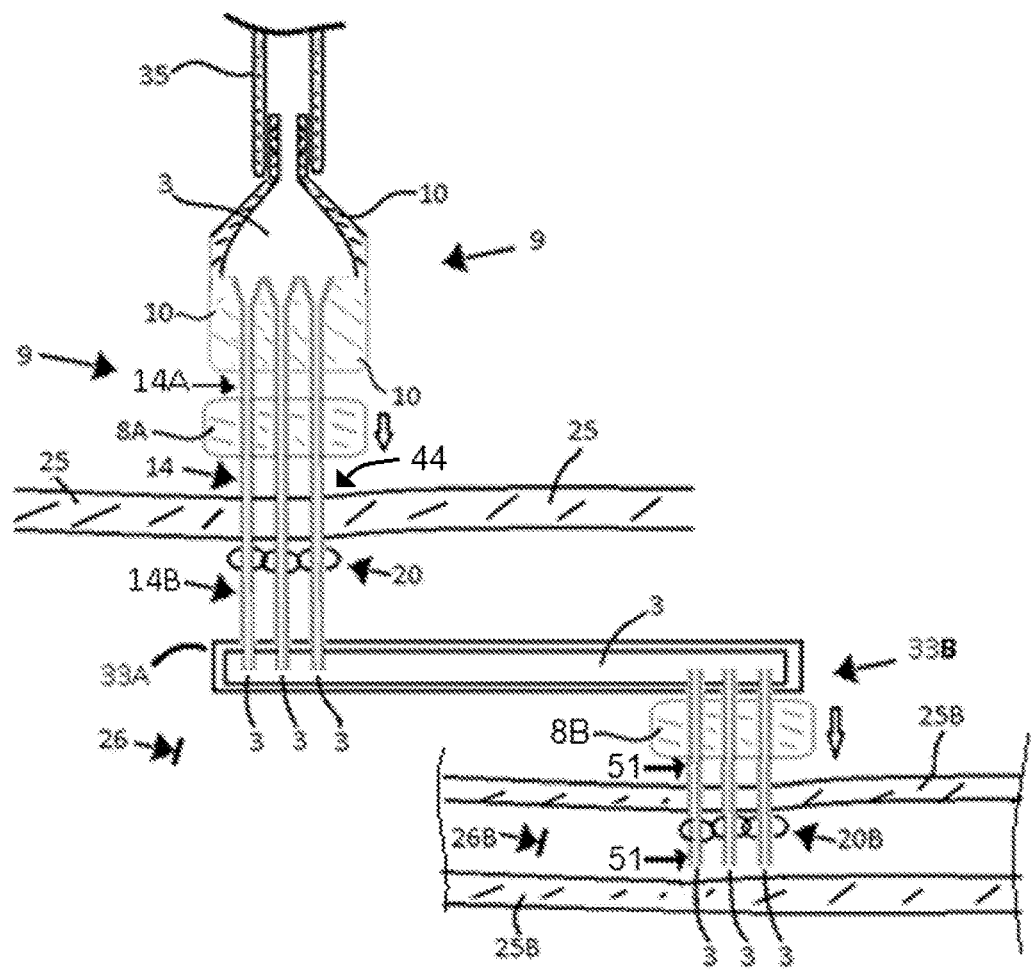
FIG. 44 is a cross sectional view of the plurality of ducts 14 comprises the fastening system 47, according to another embodiment of the invention.

FIG. 44 is a cross sectional view of the plurality of ducts 14 that comprises the fastening system 47, according to another embodiment of the invention.

In another characteristic of this embodiment, the embodiment is fastening in the patients' circulatory system 26B with balloons 20 which are blown up by ducts 14 which run parallel to the plurality of ducts 14 for external inflation of the balloons 20. In another characteristic of this embodiment, the plurality of second ends 14B are adapted to connect in the proximal portion 33A. In another characteristic of this embodiment, the distal portion 33B has the plurality of pipe 51 for piercing the cardiovascular tissue 25B to perforate 44 the patients' circulatory system 26B. In another characteristic of this embodiment, each plurality of pipe 51 has the fixation system with the proximal balloons 20B inside the patients' circulatory system 26. Some embodiments have another balloon 20 positioned outside the cardiovascular tissue 25B.

Figure 45:
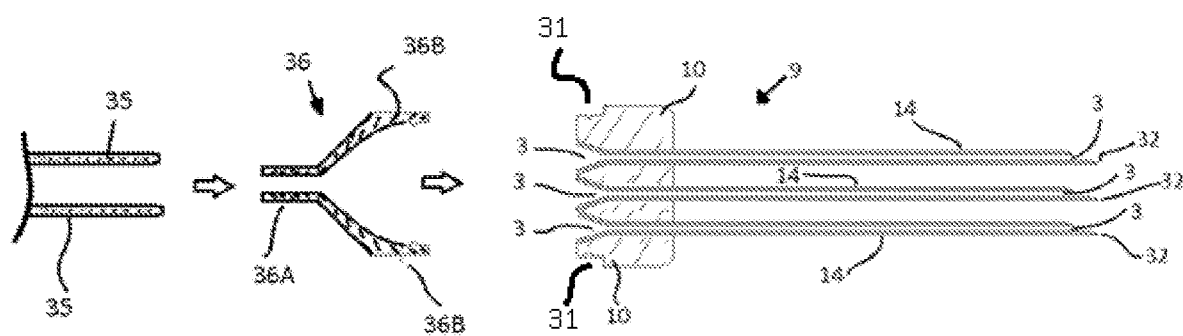
FIG. 45 is a cross sectional view of the cardiovascular cannula 50 assembly for insertion into the surgical site 26 through the plurality of transfixions 44 in tissue 25, according to another embodiment of the invention.

FIG. 45 is a cross sectional view of the cardiovascular cannula 50 assembly for insertion into the surgical site 26 through the plurality of transfixions 44 in tissue 25, according to another embodiment of the invention.

In another characteristic of this embodiment, the embodiment includes the holder 10 to connect to the extracorporeal circulation apparatus 35 hose; the plurality of ducts 14 connected to the holder 10 to allow blood flow through the plurality of blood passageways 3 through the tissue 25. In another characteristic of this embodiment, the external connection 36 connects to the extracorporeal circulation apparatus 35 hose in a detachable manner. In another characteristic of this embodiment, the external connection 36 is adapted to detachably connect the socket 31. In another characteristic of this embodiment, the holder 10 connects to the external connection 36 in a sealing and detachable manner, to prevent blood leakage and air to input in the blood passageways 3. In another characteristic of this embodiment, the plurality of ducts 14 are adapted to connect to the connection 36 or to the patients' circulatory system 26B.

Figure 46:
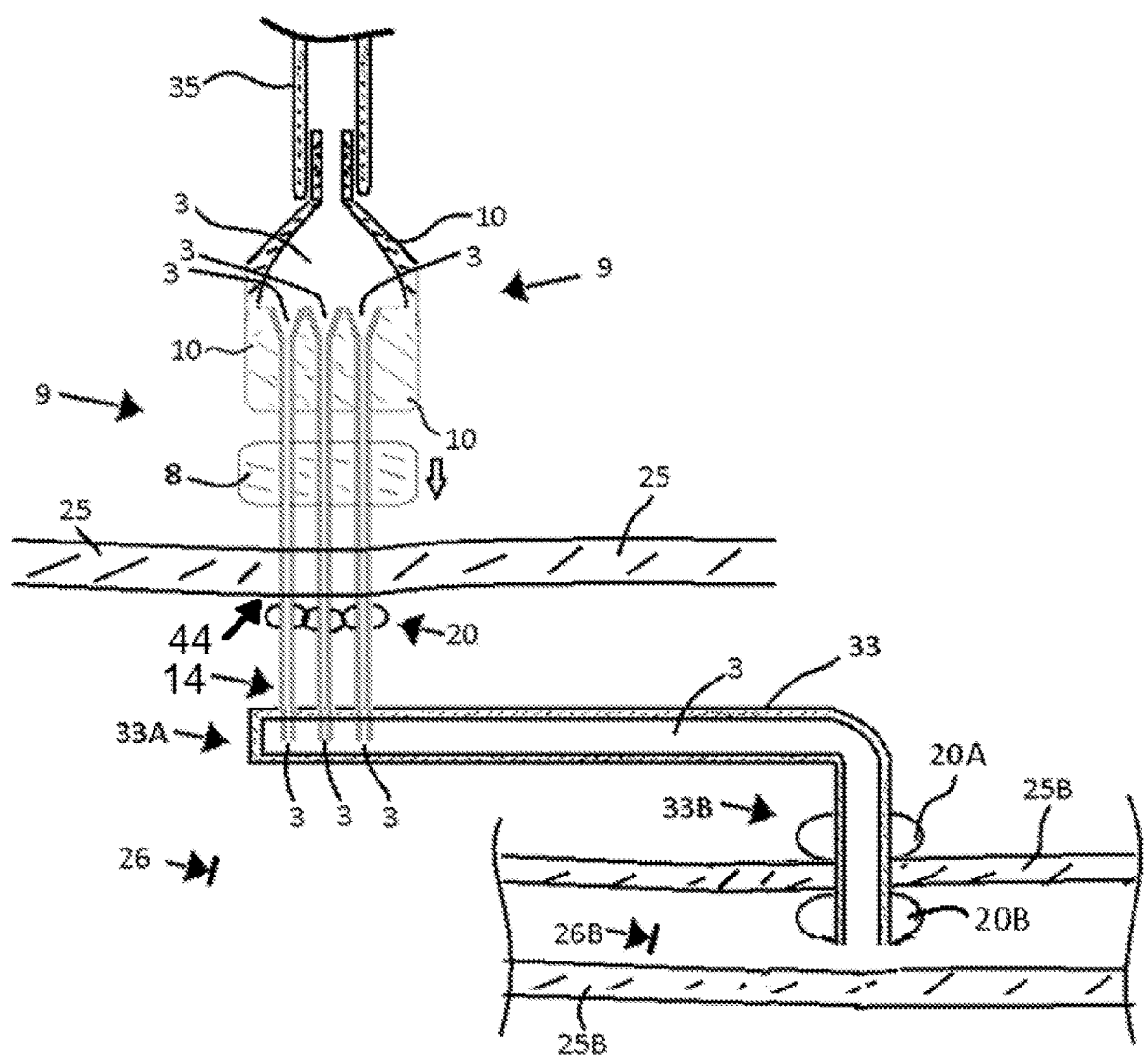
FIG. 46 is a cross sectional view of the cardiovascular cannula 50 assembly for extracorporeal blood circulation by the plurality of transfixions 44 through the tissue 25 according to another embodiment of the invention.

FIG. 46 is a cross sectional view of the cardiovascular cannula 50 assembly for extracorporeal blood circulation by the plurality of transfixions 44 through the tissue 25 according to another embodiment of the invention.

In another characteristic of this embodiment, the embodiment includes: the holder 10 to connect to the extracorporeal circulation apparatus 35 hose and the plurality of ducts 14 connected to the holder 10 to allow blood flow through the plurality of blood passageways 3. In another characteristic of this embodiment, the plurality of ducts 14 is connected to the proximal portion 33A of the internal connection 33. In another characteristic of this embodiment, the distal portion 33B of the internal connection 33 is connected to the patients' circulatory system 26B through the cardiovascular tissue 25B. In another characteristic of this embodiment, a proximal balloon 20A serves as a stop for the distal portion 33B inlet in the patients' circulatory system 26B. In another characteristic of this embodiment, the distal portion 33B has a second balloon 20B inside the patients' circulatory system 26B. In some embodiments, there is no second balloon 20B. In some embodiments, there is no proximal balloon 20A. In some embodiments, there is no balloon 20.

Figure 47:
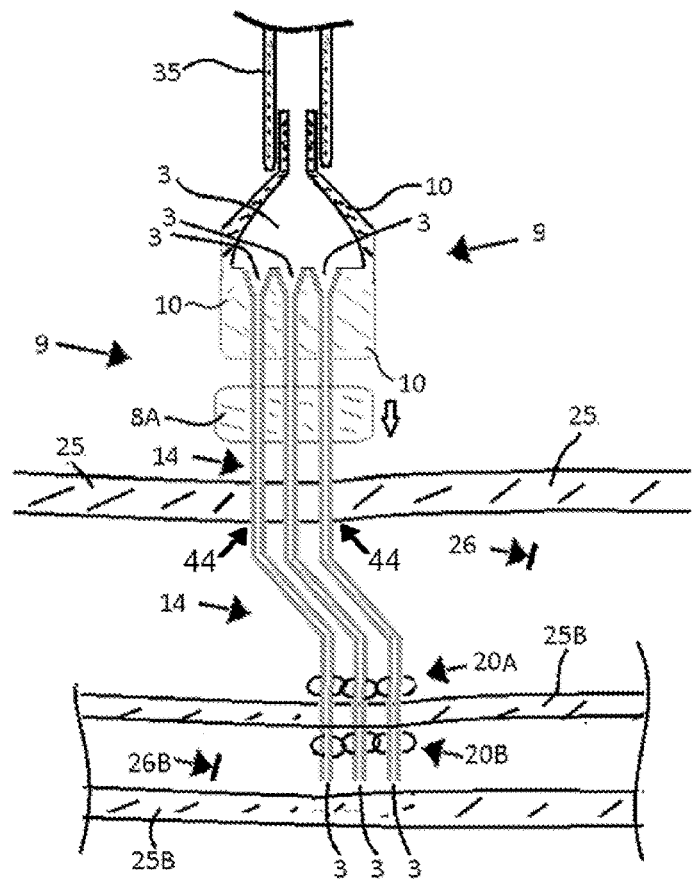
FIG. 47 is a cross sectional view of the cardiovascular cannula 50 assembly for extracorporeal blood circulation by the plurality of transfixions 44 through the tissue 25 according to another embodiment of the invention.

FIG. 47 is a cross sectional view of the cardiovascular cannula 50 assembly for extracorporeal blood circulation by the plurality of transfixions 44 through the tissue 25, according to another embodiment of the invention.

This embodiment includes: the holder 10 to connect to the extracorporeal circulation apparatus 35 hose; the plurality of ducts 14 connected to the holder 10 to allow blood flow through the plurality of blood passageways 3 to the patients' circulatory system 26B, through the tissue 25 and through the cardiovascular tissue 25B. In another characteristic of this embodiment, the plurality of ducts 14 is made of flexible material. In another characteristic of this embodiment, the holder 10 connects to the extracorporeal circulation apparatus 35 hose in a detachable manner. In another characteristic of this embodiment, the holder 10 connects to the extracorporeal circulation apparatus 35 hose in a sealing manner, to prevent blood leakage and air to input in the blood passageways 3. In another characteristic of this embodiment, the plurality of ducts 14 is adapted to connect to the patients' circulatory system 26B. In another characteristic of this embodiment, the plurality of ducts 14 have the fastening system 47 in cardiovascular tissue 25B, there is a distal balloon 25B within the patients' circulatory system 26B and another proximal balloon 20A outside the cardiovascular tissue 25B. In another characteristic of this embodiment, the proximal balloon 20A and the second balloon 20B is inflated and deflated externally by ducts 14. In another characteristic of this embodiment, the balloon 20 and each second balloon 20B is connected to the tube passing through the wall of the ducts 14 and is externalized in the holder 10.

Figure 48:
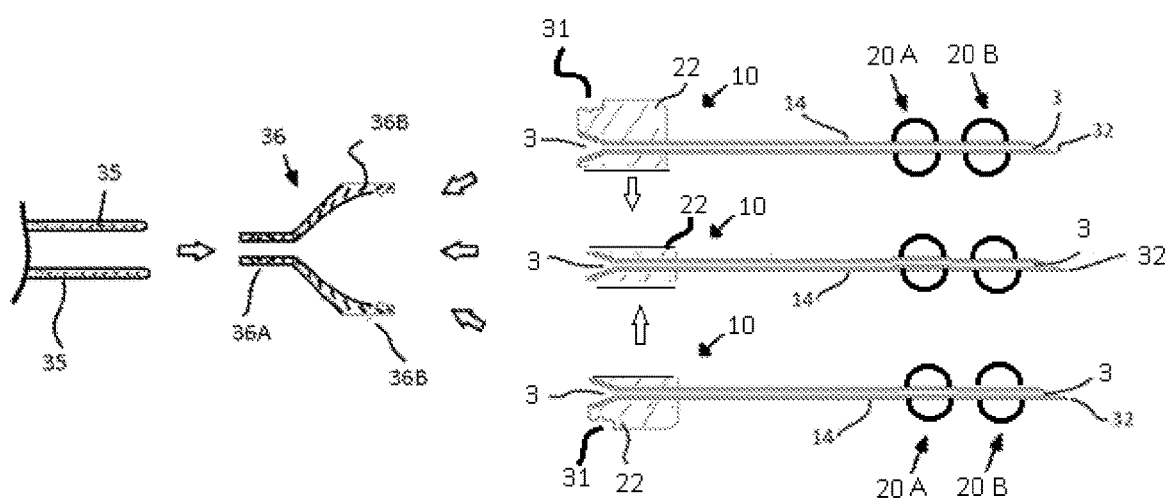
FIG. 48 is a side view of another modular embodiment of the invention.

FIG. 48 is a side view of another modular embodiment of the invention.

In another characteristic of this embodiment, the plurality of ducts 14 is made of flexible material. In another characteristic of this embodiment, the plurality of ducts 14 is made to be positioned, one at a time, at the patients' circulatory system 26B, with the aid of the mandrel 1. In another characteristic of this embodiment, the balloons 20 are inflating through ducts 14 which pass into the wall of the plurality of ducts 14. In another characteristic of this embodiment, the second balloon 20 B is adapted to be positioned at the patients' circulatory system 26B, the proximal balloon 20A is adapted to be positioned externally of the cardiovascular tissue 25B. The blocks 22 are adapted to be joined together outside the surgical site 26. In another characteristic of this embodiment, the holder 10 is adapted to connect to the external connection 36. In some embodiments, the external connection 36 is modular, there is one external connection 36 for each block 22. In some embodiments, each block 22 is adapted to connect to the external connection 36 in a separate way. The arrows show the direction in which the modular parts connect. In another characteristic of this embodiment, each proximal balloon 20A and each second balloon 20B is inflated and deflated externally by ducts 14. In another characteristic of this embodiment, each proximal balloon 20A and each second balloon 20B is connected to the tube passing through the wall of the ducts 14 and is externalized in the holder 10.

Figure 49:
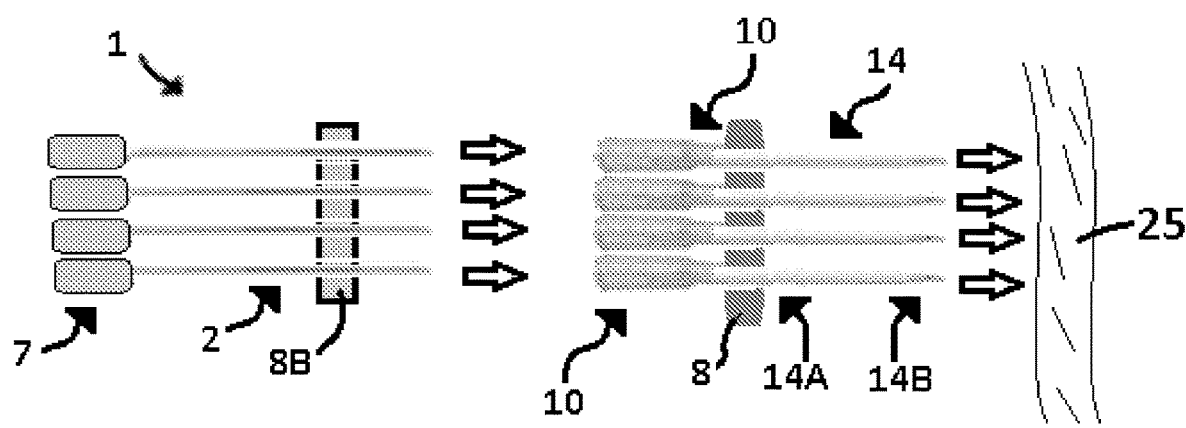
FIG. 49 It is a lateral view of the mandrel 1 with handle 7 modular, and the middle part 9 with the plurality of modular holders 10, according to another embodiment of the invention.

FIG. 49 It is a lateral view of the mandrel 1 with the handle 7 modular and the middle part 9 with the plurality of modular holders 10, according to another embodiment of the invention.

In another characteristic of this embodiment, the protector guide 8 maintains the plurality of the middle part 9 together. In another characteristic of this embodiment, middle 9 part is adapted to be able to connect and disconnect to the protector guide 8. In another characteristic of this embodiment, modular middle part 9 is adapted to be removed and replaced. In another characteristic of this embodiment, the middle parts 9 are interconnectable. In another characteristic of this embodiment, there are four modular handle 7. In another characteristic of this embodiment, the protector guide 8B keeps the piercing tips 2 together. In another characteristic of this embodiment, the protector guide 8B is adapted to connect disconnectedly to the middle part 9.

Figure 50:
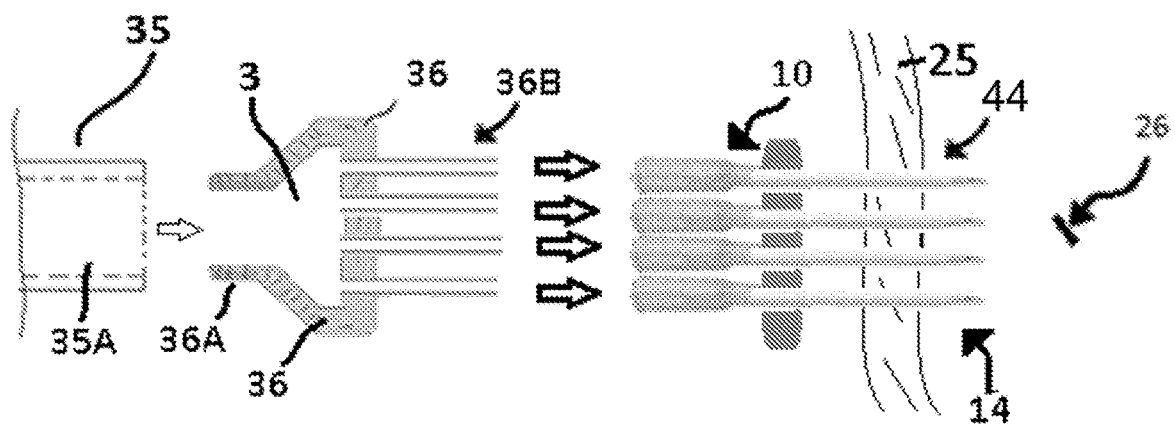
FIG. 50 is a lateral view of the middle part 9 with the plurality of modular holders 10 and the plurality of distal end 36B, according to another embodiment of the invention.

FIG. 50 is a lateral view of the middle part 9 with the plurality of modular holders 10 and the plurality of distal ends 36B, according to another embodiment of the invention. In another characteristic of this embodiment, the four distal ends 36B are ready to be inserted in the four holders 10. In another characteristic of this embodiment, the extracorporeal circulation apparatus 35 hose is ready to be connected in the proximal end 36A. The second end 14B is within the surgical site 26. The arrows show the direction of connection.

It will be apparent to one skilled in the art that the invention may be provided including some or all the mentioned features and components without departing from the spirit and scope of the invention. For purposes of comparing some embodiments of the invention, certain aspects and advantages of these embodiments are described. Not necessarily all such aspects or advantages are achieved by any particular embodiment. Thus, for example, some embodiments can be carried out in a manner that achieves or optimizes one advantage or group of advantages as described, herein without necessarily achieving another aspects or advantages as can also be described or suggested herein. It will also be apparent to the skilled artisan that the embodiments described above are specific examples of a broader invention which may have greater scope than any of the singular descriptions taught. There may be many alterations made in the descriptions without departing from the spirit scope of the invention. Although, certain preferred embodiments and examples are disclosed, inventive subject matter extends beyond the specifically disclosed embodiments to another alternative embodiments and/or uses, and to modifications and equivalents thereof. Thus, the scope of the claims appended hereto is not limited by any of the particular embodiments described. For example, in any method or process disclosed herein, the acts or operations of the method or process can be performed in any suitable sequence, and they are not necessarily limited to any particular disclosed sequence. Some operations can be described as multiple discrete operations in turn, in a manner that can be helpful in understanding certain embodiments, however, the order of description should not be construed to imply that these operations are order dependent.

I claim:

1. A cardiovascular cannula 50 for connecting an extracorporeal circulation apparatus 35 to the patients' circulatory system 26B for providing extracorporeal blood circulation through a plurality of transfixions 44 in a tissue 25 space apart by a distance [FIG. 2, FIG. 44, FIGS. 46-47], comprising: a holder 10; and the plurality of ducts 14 connected to said holder 10; wherein said holder 10 is adapted to connect to the extracorporeal circulation apparatus 35; wherein at least one of said plurality of ducts 14 is adapted to connect to the patients' circulatory system 26B; wherein said holder 10 and said plurality of ducts 14 includes blood passageways; and a mandrel 1, and said mandrel 1 including a plurality of piercing tips 2 connected to a handle 7, wherein said mandrel 1 detachably engages said cardiovascular cannula 50 forming a single inserting trocar set 42.

2. The cardiovascular cannula of claim 1, wherein at least one of said plurality of ducts 14 is adapted to connect to an internal connection 33 in the surgical site 26.

3. A cardiovascular cannula 50 for extracorporeal blood circulation connecting an extracorporeal circulation apparatus 35 to the patients' circulatory system 26B through a plurality of transfixions 44 in a tissue 25 space apart by a distance, comprising: a holder 10; said plurality of ducts 14 connected to said holder 10; and an internal connection 33, said internal connection 33 including a proximal portion 33A and a distal portion 33B; wherein said distal portion 33B is adapted to connect to the patients' circulatory system 26B; wherein said proximal portion 33A is connectable to said ducts 14; wherein said holder 10, said ducts 14 and said internal connection 33 includes blood passageways 3.

4. The cardiovascular cannula of claim 3, wherein said holder 10 is modular and includes an external connection 36, said external connection 36 including a proximal end 36A and a distal end 36B, said proximal end 36A adapted to connect to the extracorporeal circulation apparatus 35, and said distal end 36B is adapted to detachably connect said holder 10.

5. The cardiovascular cannula of claim 3, wherein said plurality of ducts 14 are adapted for insertion through a trocar 42 containing a plurality of access port 49.

6. The cardiovascular cannula of claim 3, wherein at least one of said plurality of ducts 14 further comprises a sharp tip 32 to transfix said tissue 25.

7. The cardiovascular cannula of claim 3, wherein each said plurality of ducts 14 includes a dilator 11.

8. The cardiovascular cannula of claim 3, wherein at least one of said plurality of ducts 14 is adapted to connect a surgical device 52 within said surgical site 26.

9. The cardiovascular cannula of claim 3, further comprising a coil 21.

10. The cardiovascular cannula of claim 3, further comprising at least one protector guide 8.

11. The cardiovascular cannula of claim 3, wherein at least one of said plurality of ducts 14 comprises a fastening system 47 in said tissue 25.

12. The cardiovascular cannula of claim 3, further comprising a retractable 4.

13. The cardiovascular cannula of claim 3, wherein said holder 10 is adapted to connect to the surgical device 52.

14. The cardiovascular cannula of claim 3, wherein said internal connection 33 is made to be inserted in a surgical site 26 through a conventional trocar 53.

15. The cardiovascular cannula of claim 3, wherein said internal connection 33 includes means to fix in the cardiovascular tissue 25B.

16. The cardiovascular cannula of claim 3, further comprising a mandrel 1 including a handle 7, and said mandrel 1 including a plurality of piercing tips 2 connected to the handle 7, wherein said mandrel 1 detachably engages said cannula 50 forming a single punch trocar set 42.

17. The cardiovascular cannula of claim 3, wherein at least one part is made in a transparent material.

18. A method of assembling the cardiovascular cannula of claim 3, comprising the steps of:
 a. connecting said plurality of ducts 14 to said internal connection 33; and
 b. disconnecting said plurality of ducts 14 from said internal connection 33.

19. The method of claim 18, further comprising the step of:
 c. engaging a mandrel 1 to said cannula 50.

* * * * *